United States Patent
Abeywardane et al.

(10) Patent No.: US 9,303,018 B2
(45) Date of Patent: Apr. 5, 2016

(54) INHIBITORS OF LEUKOTRIENE PRODUCTION

(71) Applicants: Asitha Abeywardane, Danbury, CT (US); John Broadwater, Southbury, CT (US); Hidenori Takahashi, Langrangeville, NY (US)

(72) Inventors: Asitha Abeywardane, Danbury, CT (US); John Broadwater, Southbury, CT (US); Hidenori Takahashi, Langrangeville, NY (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/330,297

(22) Filed: Jul. 14, 2014

(65) Prior Publication Data

US 2015/0018333 A1  Jan. 15, 2015

Related U.S. Application Data

(60) Provisional application No. 61/846,137, filed on Jul. 15, 2013.

(51) Int. Cl.
*C07D 401/14* (2006.01)
*A61K 31/4709* (2006.01)
*A61K 31/496* (2006.01)

(52) U.S. Cl.
CPC .......... *C07D 401/14* (2013.01); *A61K 31/4709* (2013.01); *A61K 31/496* (2013.01)

(58) Field of Classification Search
CPC . C07D 401/14; A61K 31/4709; A61K 31/496
See application file for complete search history.

(56) References Cited

U.S. PATENT DOCUMENTS

| | | | |
|---|---|---|---|
| 4,918,092 | A | 4/1990 | Frenette et al. |
| 5,120,758 | A | 6/1992 | Satoh |
| 6,180,637 | B1 | 1/2001 | Schindler et al. |
| 7,098,222 | B2 | 8/2006 | Altenbach et al. |
| 7,429,665 | B2 | 9/2008 | Verhoest et al. |
| 7,674,802 | B2 | 3/2010 | Sandanayaka et al. |
| 8,551,982 | B2 | 10/2013 | Abeywardane et al. |
| 8,946,203 | B2 | 2/2015 | Abeywardane et al. |
| 2002/0132822 | A1 | 9/2002 | Noe et al. |
| 2006/0019269 | A1 | 1/2006 | Helgadottir et al. |
| 2006/0223792 | A1 | 10/2006 | Butler et al. |
| 2007/0066820 | A1 | 3/2007 | Sandanayaka et al. |
| 2007/0149544 | A1 | 6/2007 | Sandanayaka et al. |
| 2013/0196973 | A1 | 8/2013 | Abeywardane et al. |
| 2013/0236468 | A1 | 9/2013 | Bylock |
| 2013/0244996 | A1 | 9/2013 | Abeywardane et al. |
| 2014/0031339 | A1 | 1/2014 | Abeywardane et al. |

FOREIGN PATENT DOCUMENTS

| | | |
|---|---|---|
| CA | 2076573 A1 | 2/1993 |
| CA | 2280727 A1 | 8/1998 |
| WO | 9610999 A2 | 4/1996 |
| WO | 9611192 A1 | 4/1996 |
| WO | 2004056369 A1 | 7/2004 |
| WO | 2007040682 A1 | 4/2007 |
| WO | 2008052086 A1 | 5/2008 |
| WO | 2011032050 * | 3/2011 |
| WO | 2011114220 A1 | 9/2011 |
| WO | 2012125598 A1 | 9/2012 |
| WO | 2013012844 A1 | 1/2013 |
| WO | 2014014874 A1 | 1/2014 |

OTHER PUBLICATIONS

Davies, D. R et al., "Discovery of Leukotriene A4 Hydrolase Inhibitors Using Metabolomics Biased Fragment Crystallography +", Journal of Medicanal Chemistry, vol. 52, No. 15, Aug. 13, 2009, pp. 4694-4715.
Grice, C.A. et al., "Current Status of Leukotriene A4 Hydrolase Inhibitors". Expert Opinion on Therapeutic Patents, vol. 18, No. 12, Dec. 1, 2008, pp. 1333-1350.
International Search Report and Written Opinion for PCT/US2012/028843 mailed May 7, 2012.
International Search Report and Written Opinion for PCT/US2013/029054 mailed May 21, 2013.
International Search Report and Written Opinion for PCT/US2013/050624 mailed Sep. 11, 2013.
International Search Report and Written Opinion for PCT/US2014/046489 mailed Sep. 9, 2014.
International Search Report and Written Opinion for PCT/US2014/046492 mailed Sep. 11, 2014.
International Search Report for PCT/EP2013/054381 mailed May 21, 2013.
International Search Report for PCT/US2012/047024 mailed Sep. 20, 2012.
Minami, M. M et al., "Molecular Cloning of a cDNA Coding for Human Leukotriene A4 Hydrolase". The Journal of Biological Chemistry, vol. 262, No. 29, 1987, pp. 13873-13876.

(Continued)

*Primary Examiner* — D M Seaman
(74) *Attorney, Agent, or Firm* — Michael P. Morris; David L. Kershner; Usha R. Patel

(57) ABSTRACT

The present invention relates to compounds of formula (I):

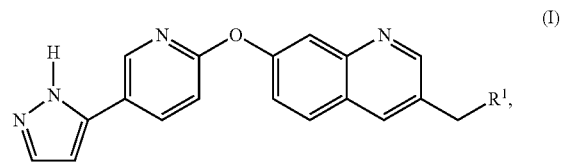

(I)

or a pharmaceutically acceptable salt thereof, wherein $R^1$ is defined herein. The compounds of formula (I) are useful as inhibitors of leukotriene $A_4$ hydrolase ($LTA_4H$) and treating $LTA_4H$ related disorders. The present invention also relates to pharmaceutical compositions comprising the compounds of formula (I), methods of using these compounds in the treatment of various diseases and disorders, and processes for preparing these compounds.

16 Claims, No Drawings

(56) References Cited

OTHER PUBLICATIONS

Sandanayaka, V. et al., "Discovery of 4-[(2 S)-2-{[4-(4-Chlorophenoxy)phenoxy]methyl}-1-pyrrolidinyl]butanoic Acid (DG-051) as a Novel Leukotriene B4 Biosynthesis". Journal of Medicinal Chemistry, vol. 53, No. 2, Jan. 28, 2010, pp. 573-585.

Sandanayaka, V. et al., "Discovery of novel leukotriene A4 hydrolase inhibitors based on piperidine and piperazine scaffolds". Bioorganice and Medicinal Chemistry Letters, Pergamon, Elsevier Science, GB, vol. 20, No. 9, May 1, 2010, pp. 2851-2854.

Thangapandian, Sundarapandian et al., "Molecular Docking and Pharacophore Filtering in the Discovery of Dual-Inhibitors for Human Leukotreine A4 Hydrolase and Leukotriene C4 Synthase", Journal of Chemical Information and Modeling, vol. 51, No. 1, Jan. 24, 2011, pp. 33-44.

* cited by examiner

INHIBITORS OF LEUKOTRIENE PRODUCTION

FIELD OF THE INVENTION

This invention relates to novel compounds that are useful as inhibitors of leukotriene $A_4$ hydrolase ($LTA_4H$) and are thus useful for treating a variety of diseases and disorders that are mediated or sustained through the activity of leukotrienes including asthma, and allergy; cardiovascular diseases including atherosclerosis, myocardial infarction and stroke; and inflammation diseases including atopic dermatitis, allergy, asthma, autoimmune diseases, Crohn's disease, cystic fibrosis, diabetic nephropathy, diabetic retinopathy, ulcerative colitis, and steatohepatitis. This invention also relates to pharmaceutical compositions comprising these compounds, methods of using these compounds in the treatment of various diseases and disorders, processes for preparing these compounds and intermediates useful in these processes.

BACKGROUND OF THE INVENTION

Leukotrienes (LT) are oxidized lipids that are produced by several cell types including neutrophils, mast cells, eosinophils, basophils, monocytes and macrophages. The first committed step in the intracellular synthesis of LTs involves oxidation of arachidonic acid by 5-lipoxygenase (5-LO) to leukotriene $A_4$ ($LTA_4$), a process requiring the 5-lipoxygenase-activating protein (FLAP). Leukotriene $A_4$ hydrolase ($LTA_4H$) catalyzes the hydrolysis of $LTA_4$ to produce leukotriene $B_4$ ($LTB_4$). Through the engagement of the $LTB_4$ receptors (BLT1, BLT2), $LTB_4$ stimulates an array of pro-inflammatory responses (leukocyte chemotaxis, cytokine release, etc.). The leukotriene pathway has been implicated in diseases in which inflammation is a critical component of the pathology; these include cancer, asthma, atherosclerosis, colitis, glomerularnephritis, and pain (for a review, see M. Peters-Golden and W. R. Henderson, Jr., M. D., N. Engl. J. Med., 2007, 357, 1841-1854).

BRIEF SUMMARY OF THE INVENTION

The present invention provides novel compounds which inhibit leukotriene $A_4$ hydrolase ($LTA_4H$) and are thus useful for treating a variety of diseases and disorders that are mediated or sustained through the activity of leukotrienes, including allergic, pulmonary, fibrotic, inflammatory and cardiovascular diseases and cancer.

In its broadest embodiment ("embodiment 1"), the invention relates to a compound of formula (I):

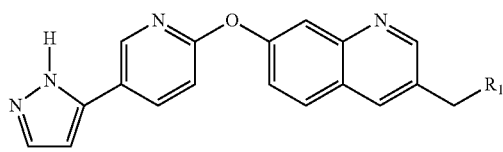

(I)

or a pharmaceutically acceptable salt thereof, wherein:
$R^1$ is:
(a) a group of formula —$N(R^2)(R^3)$, wherein
$R^2$ is selected from the group consisting of hydrogen, —$(C_1-C_6)$alkyl, and —$(C_3-C_6)$cycloalkyl;

$R^3$ is selected from the group consisting of hydrogen, —$(C_1-C_6)$alkyl, —$(C_3-C_6)$cycloalkyl, and -(4- to 7-membered)heterocyclyl,
wherein each of said —$(C_1-C_6)$alkyl, —$(C_3-C_6)$cycloalkyl, and -(4- to 7-membered)heterocyclyl of said $R^3$ may optionally be substituted by 1 to 3 groups independently selected from the group consisting of $R^4$, —(($C_1-C_6$)alkylene)-$R^4$, —C(O)—($C_1-C_6$)alkyl, —C(O)—($C_3-C_6$)cycloalkyl, and —C(O)—(($C_1-C_6$) alkylene)-$R^4$;
$R^4$ is selected from the group consisting of halo, —OH, =O, —$NH_2$, —NH($C_1-C_6$)alkyl, —N(($C_1-C_6$)alky)$_2$, —($C_1-C_6$)alkyl, —O($C_1-C_6$)alkyl, —($C_3-C_6$)cycloalkyl, and -(4- to 7-membered)heterocyclyl);
wherein each of said $R^4$ may optionally be substituted by 1 to 3 groups independently selected from the group consisting of —O($C_1-C_6$)alkyl, and —($C_3-C_6$)cycloalkyl;
or
(b) a 4- to 9-membered N-heterocyclic ring of formula:

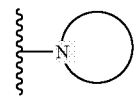

wherein said 4- to 9-membered N-heterocyclic ring optionally comprises one to three additional hetero-ring atoms selected from the group consisting of nitrogen, oxygen and sulfur atoms; and wherein said 4- to 9-membered N-heterocyclic ring is optionally substituted by 1 to 3 groups independently selected from the group consisting of $R^5$, —(($C_1-C_6$)alkylene)-$R^5$, —C(O)—($C_1-C_6$) alkyl, —C(O)—($C_3-C_6$)cycloalkyl, —C(O)—(($C_1-C_6$) alkylene)-$R^5$, —C(O)—N($R^6$)—(($C_1-C_6$)alkylene)-$R^5$, —C(O)—N($R^6$)($R^6$) and -(4- to 7-membered)heterocyclyl) optionally substituted by 1 to 3 $R^5$ groups;
each $R^5$ is independently selected from the group consisting of halo, —OH, =O, —N($R^6$)$_2$, —N($R^6$)(C(O)—$R^6$), —($C_1-C_6$)alkyl, —O($C_1-C_6$)alkyl, —($C_3-C_6$)cycloalkyl, and -(4- to 7-membered)heterocyclyl); and
each $R^6$ is independently selected from the group consisting of hydrogen and —($C_1-C_6$)alkyl optionally substituted by —OH.

In a second embodiment (embodiment 2), the invention relates to a compound of embodiment 1, or a pharmaceutically acceptable salt thereof, wherein $R^1$ is a group of formula —$N(R^2)(R^3)$, and wherein $R^2$ is —($C_1-C_6$)alkyl.

In a third embodiment (embodiment 3), the invention relates to a compound of any one of the preceding embodiments, or a pharmaceutically acceptable salt thereof, wherein $R^1$ is a group of formula —$N(R^2)(R^3)$, and wherein $R^3$ is a -(4- to 7-membered)heterocyclyl optionally substituted by 1 to 3 groups independently selected from the group consisting of $R^4$, —(($C_1-C_6$)alkylene)-$R^4$, —C(O)—($C_1-C_6$)alkyl, —C(O)—($C_3-C_6$)cycloalkyl, and —C(O)—(($C_1-C_6$)alkylene)-$R^4$.

In a fourth embodiment (embodiment 4), the invention relates to a compound of any one of the preceding embodiments, or a pharmaceutically acceptable salt thereof, wherein
$R^1$ is a group of formula —$N(R^2)(R^3)$, and wherein
$R^2$ is —($C_1-C_6$)alkyl; and
$R^3$ is pyrrolidinyl optionally substituted by 1 to 3 groups independently selected from the group consisting of —OH and —C(O)—($C_1-C_6$)alkylene)-OH.

In a fifth embodiment (embodiment 5), the invention relates to a compound of any one of the preceding embodiments, or a pharmaceutically acceptable salt thereof, wherein $R^1$ is a group of formula —$N(R^2)(R^3)$, and wherein $R^2$ is methyl; and $R^3$ is pyrrolidinyl substituted by —C(O)—$(C_1$-$C_6)$alkylene)-OH.

In a sixth embodiment (embodiment 6), the invention relates to a compound of any one of embodiments 1 and 2 described above, or a pharmaceutically acceptable salt thereof, wherein $R^1$ is a group of formula —$N(R^2)(R^3)$, and wherein $R^2$ is —$(C_1$-$C_6)$alkyl, and $R^3$ is —$(C_1$-$C_6)$alkyl optionally substituted by 1 to 3 groups independently selected from the group consisting of $R^4$, —$((C_1$-$C_6)$alkylene)-$R^4$, —C(O)—$(C_1$-$C_6)$alkyl, and —C(O)—$((C_1$-$C_6)$alkylene)-$R^4$.

In a seventh embodiment (embodiment 7), the invention relates to a compound of any one of embodiments 1, 2 and 6 described above, or a pharmaceutically acceptable salt thereof, wherein $R^1$ is a group of formula —$N(R^2)(R^3)$, and wherein $R^2$ is —$(C_1$-$C_6)$alkyl, and $R^3$ is —$(C_1$-$C_6)$alkyl optionally substituted by a -(4- to 7-membered)heterocyclyl), wherein said -(4- to 7-membered)heterocyclyl) is optionally substituted by 1 to 3 groups independently selected from the group consisting of —C(O)—$(C_1$-$C_6)$alkyl, and —C(O)—$(C_3$-$C_6)$cycloalkyl.

In an eighth embodiment (embodiment 8), the invention relates to a compound of any one of embodiments 1, 2, 6 and 7 described above, or a pharmaceutically acceptable salt thereof, wherein $R^1$ is a group of formula —$N(R^2)(R^3)$, and wherein $R^2$ is methyl, and $R^3$ is methyl substituted by a -(4- to 7-membered)heterocyclyl), wherein said -(4- to 7-membered)heterocyclyl) is substituted by 1 to 2 groups independently selected from the group consisting of —C(O)—$(C_1$-$C_6)$alkyl.

In a ninth embodiment (embodiment 9), the invention relates to a compound of embodiment 1, or a pharmaceutically acceptable salt thereof, wherein $R^1$ is a 4- to 9-membered N-heterocyclic ring, and wherein said 4- to 9-membered N-heterocyclic ring is optionally substituted by 1 to 3 groups independently selected from the group consisting of $R^5$, —$((C_1$-$C_6)$alkylene)-$R^5$, —C(O)—$(C_1$-$C_6)$alkyl, —C(O)—$(C_3$-$C_6)$cycloalkyl, —C(O)—$((C_1$-$C_6)$alkylene)-$R^5$, —C(O)—$N(R^6)$—$((C_1$-$C_6)$alkylene)-$R^5$, —C(O)—$N(R^6)(R^6)$ and -(4- to 7-membered)heterocyclyl).

In an tenth embodiment (embodiment 10), the invention relates to a compound of any one of embodiments 1 and 9 above, or a pharmaceutically acceptable salt thereof, wherein $R^1$ is a 4- to 9-membered N-heterocyclic ring selected from the group consisting of azetidinyl, pyrrolidinyl, piperidinyl, and piperazinyl; wherein each of said azetidinyl, pyrrolidinyl, piperidinyl, and piperazinyl is optionally substituted by 1 to 3 groups independently selected from the group consisting of $R^5$, —$((C_1$-$C_6)$alkylene)-$R^5$, —C(O)—$(C_1$-$C_6)$alkyl, —C(O)—$(C_3$-$C_6)$cycloalkyl, —C(O)—$((C_1$-$C_6)$alkylene)-$R^5$, —C(O)—$N(R^6)$—$((C_1$-$C_6)$alkylene)-$R^5$, —C(O)—$N(R^6)(R^6)$ and -(4- to 7-membered)heterocyclyl).

In an eleventh embodiment (embodiment 11), the invention relates to a compound of any one of embodiments 1, 9 and 10 above, or a pharmaceutically acceptable salt thereof, wherein $R^1$ is selected from the group consisting of:

an azetidinyl substituted by 1 to 3 groups selected from the group consisting of —OH, —$(C_1$-$C_6)$alkyl and —C(O)—$(C_1$-$C_6)$alkyl;

a pyrrolidinyl substituted by 1 to 3 groups selected from the group consisting of —OH, —C(O)—$((C_1$-$C_6)$alkylene)-OH and —$N((C_1$-$C_6)$alkyl)-C(O)—$(C_1$-$C_6)$alkylene)-OH;

a piperidinyl substituted by 1 to 3 groups selected from the group consisting of —OH, —C(O)—$((C_1$-$C_6)$alkylene)-OH, —C(O)—$N((C_1$-$C_6)$alkyl)_2$, —$N((C_1$-$C_6)$alkyl)-C(O)—$(C_1$-$C_6)$alkylene)-OH, pyrrolidinyl optionally substituted by —OH and (=O), oxazolidinonyl; and a piperazinyl substituted by 1 to 3 groups selected from the group consisting of —C(O)—$(C_1$-$C_6)$alkyl, —C(O)—$(C_3$-$C_6)$cycloalkyl, —C(O)—$((C_1$-$C_6)$alkylene)-OH, and —C(O)—$((C_1$-$C_6)$alkylene)-O—$(C_1$-$C_6)$alkyl).

DETAILED DESCRIPTION OF THE INVENTION

Definitions

AIBN=azobisisobutyronitrile
BOC=tert-butyloxycarbonyl
BnO=benzyloxide
DCM=dichloromethane
DDQ=2,3-dichloro-5,6-dicyano-1,4-benzoquinone
DEA=diethylamine
DIBAL-H=diisobutylaluminum hydride
DIPEA=diisopropylethylamine
DMA=dimethylacetamide
DMAP=4-dimethylaminopyridine
DME=dimethoxyethane
DMF=dimethylformamide
DMSO=dimethylsulfoxide
$Et_2O$=ethylether
EtOAc=ethyl acetate
EtOH=ethanol
IPA=isopropyl alcohol
LDA=lithium diisopropylamide
mCPBA=meta-chloroperoxybenzoic acid
MeCN=acetonitrile
MeOH=methanol
MP-TSOH=polymer-supported toluenesulfonic acid resin
MTBE=methyl tert-butyl ether
NBS=N-bromosuccinimide
NMP=N-methylpyrrolidinone
PG=protecting group
PyBrop=bromo-tris-pyrrolidino phosphoniumhexafluorophosphate
PL-$HCO_3$=polymer-bound tetraalkylammoniumcarbonate resin
PS-DIEA=polymer-supported N,N-diisopropylethylamine resin
SEM=2-(trimethylsilyl)ethoxymethyl
TBAF=tetra-n-butylammonium fluoride
TBDPSCl=t-butyldiphenylsilyl chloride
TBTU=2-(1H-benzotriazole-1-yl)-1,1,3,3-tetramethyluronium tetrafluoroborate
TEA=triethylamine
TFA=trifluoroacetic acid
THF=tetrahydrofuran
TIPSO=triisopropylsiloxy It will be understood that the terms "compounds of formula (I)" and "compounds of the invention" have the same meaning unless indicated otherwise.

The following are representative compounds of the invention which were made by the general synthetic schemes, the examples, and known methods in the art.

TABLE 1

Examples of compounds of the invention.

| Ex. | Structure | Compound Name |
|---|---|---|
| 1 | 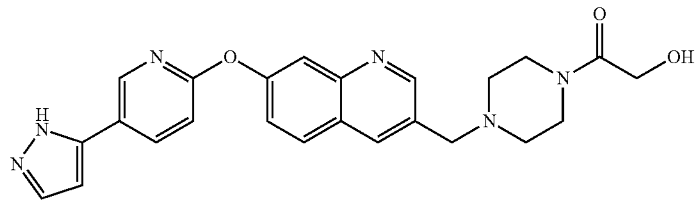 [SMILES: O=C(CO)N1CCN(Cc2cnc3cc(Oc4ccc(-c5ccn[nH]5)cn4)ccc3c2)CC1] | 2-Hydroxy-1-(4-{7-[5-(2H-pyrazol-3-yl)-pyridin-2-yloxy]-quinolin-3-ylmethyl}-piperazin-1-yl)-ethanone |
| 2 | 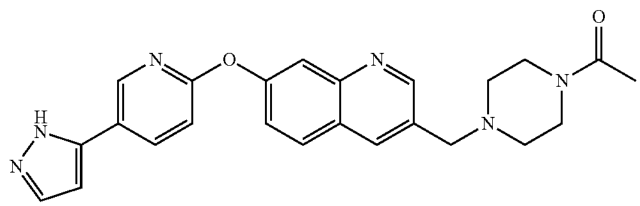 [SMILES: CC(=O)N1CCN(Cc2cnc3cc(Oc4ccc(-c5ccn[nH]5)cn4)ccc3c2)CC1] | 1-(4-{7-[5-(2H-Pyrazol-3-yl)-pyridin-2-yloxy]-quinolin-3-ylmethyl}-piperazin-1-yl)-ethanone |
| 3 | 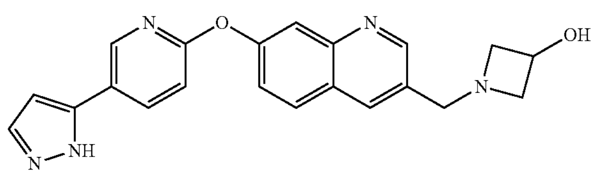 [SMILES: OC1CN(Cc2cnc3cc(Oc4ccc(-c5ccn[nH]5)cn4)ccc3c2)C1] | 1-{7-[5-(2H-Pyrazol-3-yl)-pyridin-2-yloxy]-quinolin-3-ylmethyl}-azetidin-3-ol |
| 4 | 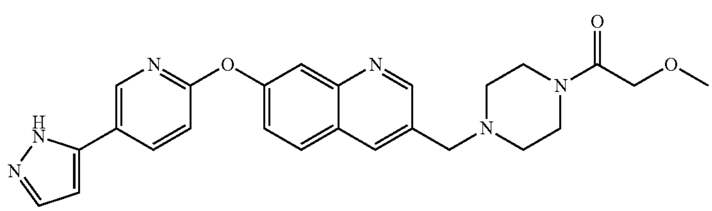 [SMILES: COCC(=O)N1CCN(Cc2cnc3cc(Oc4ccc(-c5ccn[nH]5)cn4)ccc3c2)CC1] | 2-Methoxy-1-(4-{7-[5-(2H-pyrazol-3-yl)-pyridin-2-yloxy]-quinolin-3-ylmethyl}-piperazin-1-yl)-ethanone |
| 5 | 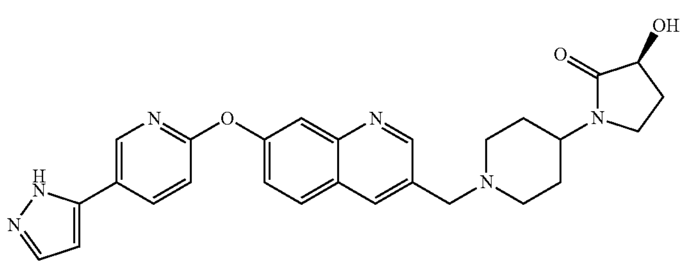 [SMILES: O=C1[C@@H](O)CCN1C1CCN(Cc2cnc3cc(Oc4ccc(-c5ccn[nH]5)cn4)ccc3c2)CC1] | (S)-3-Hydroxy-1-(1-{7-[5-(2H-pyrazol-3-yl)-pyridin-2-yloxy]-quinolin-3-ylmethyl}-piperidin-4-yl)-pyrrolidin-2-one |
| 6 | 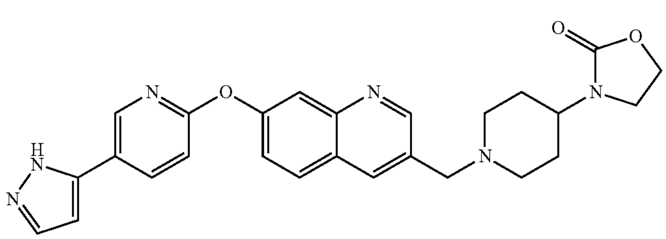 [SMILES: O=C1OCCN1C1CCN(Cc2cnc3cc(Oc4ccc(-c5ccn[nH]5)cn4)ccc3c2)CC1] | 3-(1-{7-[5-(2H-Pyrazol-3-yl)-pyridin-2-yloxy]-quinolin-3-ylmethyl}-piperidin-4-yl)-oxazolidin-2-one |
| 7 | 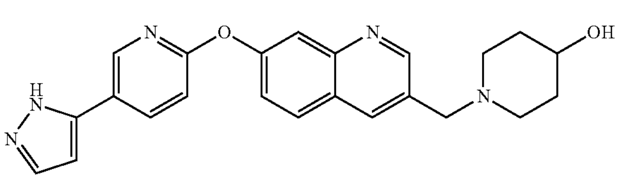 [SMILES: OC1CCN(Cc2cnc3cc(Oc4ccc(-c5ccn[nH]5)cn4)ccc3c2)CC1] | 1-{7-[5-(2H-Pyrazol-3-yl)-pyridin-2-yloxy]-quinolin-3-ylmethyl}-piperidin-4-ol |

TABLE 1-continued

Examples of compounds of the invention.

| Ex. | Structure | Compound Name |
|---|---|---|
| 8 | 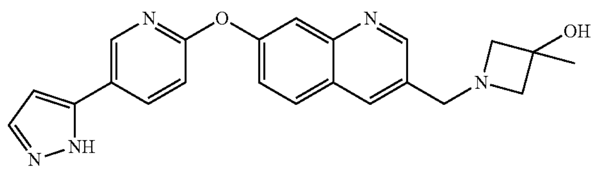 [SMILES: CC1(O)CN(Cc2cnc3cc(Oc4ccc(-c5ccn[nH]5)cn4)ccc3c2)C1] | 3-Methyl-1-{7-[5-(2H-pyrazol-3-yl)-pyridin-2-yloxy]-quinolin-3-ylmethyl}-azetidin-3-ol |
| 9 | 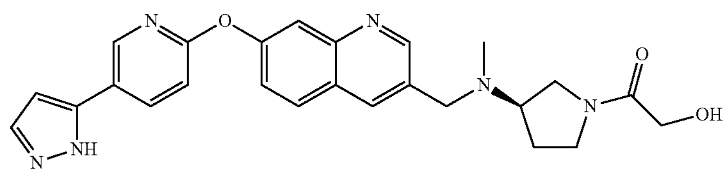 [SMILES: CN(Cc1cnc2cc(Oc3ccc(-c4ccn[nH]4)cn3)ccc2c1)[C@@H]1CCN(C(=O)CO)C1] | 2-Hydroxy-1-[(R)-3-(methyl-{7-[5-(2H-pyrazol-3-yl)-pyridin-2-yloxy]-quinolin-3-ylmethyl}-amino)-pyrrolidin-1-yl]-ethanone |
| 10 | 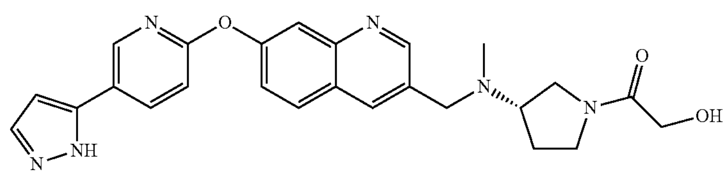 [SMILES: CN(Cc1cnc2cc(Oc3ccc(-c4ccn[nH]4)cn3)ccc2c1)[C@H]1CCN(C(=O)CO)C1] | 2-Hydroxy-1-[(S)-3-(methyl-{7-[5-(2H-pyrazol-3-yl)-pyridin-2-yloxy]-quinolin-3-ylmethyl}-amino)-pyrrolidin-1-yl]-ethanone |
| 11 | 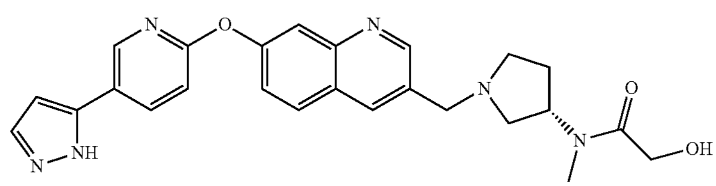 [SMILES: CN(C(=O)CO)[C@H]1CCN(Cc2cnc3cc(Oc4ccc(-c5ccn[nH]5)cn4)ccc3c2)C1] | 2-Hydroxy-N-methyl-N-((S)-1-{7-[5-(2H-pyrazol-3-yl)-pyridin-2-yloxy]-quinolin-3-ylmethyl}-pyrrolidin-3-yl)-acetamide |
| 12 | 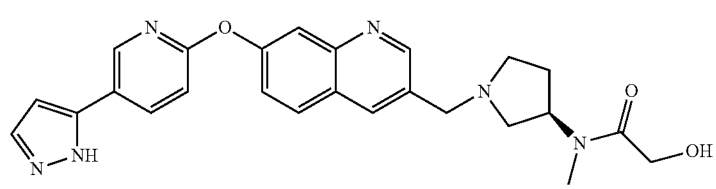 [SMILES: CN(C(=O)CO)[C@@H]1CCN(Cc2cnc3cc(Oc4ccc(-c5ccn[nH]5)cn4)ccc3c2)C1] | 2-Hydroxy-N-methyl-N-((R)-1-{7-[5-(2H-pyrazol-3-yl)-pyridin-2-yloxy]-quinolin-3-ylmethyl}-pyrrolidin-3-yl)-acetamide |
| 13 | 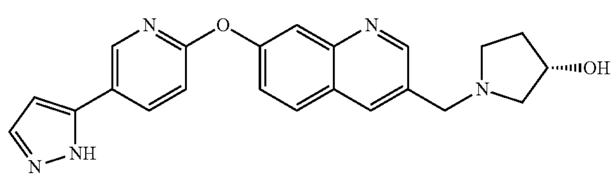 [SMILES: O[C@H]1CCN(Cc2cnc3cc(Oc4ccc(-c5ccn[nH]5)cn4)ccc3c2)C1] | (S)-1-{7-[5-(2H-Pyrazol-3-yl)-pyridin-2-yloxy]-quinolin-3-ylmethyl}-pyrrolidin-3-ol |
| 14 | 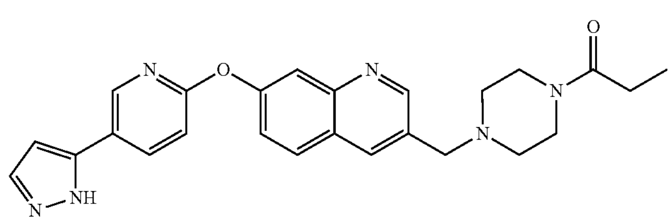 [SMILES: CCC(=O)N1CCN(Cc2cnc3cc(Oc4ccc(-c5ccn[nH]5)cn4)ccc3c2)CC1] | 1-(4-{7-[5-(2H-Pyrazol-3-yl)-pyridin-2-yloxy]-quinolin-3-ylmethyl}-piperazin-1-yl)-propan-1-one |
| 15 | 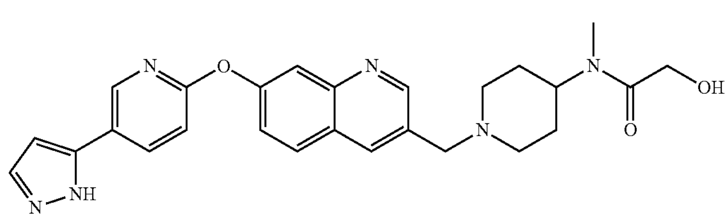 [SMILES: CN(C(=O)CO)C1CCN(Cc2cnc3cc(Oc4ccc(-c5ccn[nH]5)cn4)ccc3c2)CC1] | 2-Hydroxy-N-methyl-N-(1-{7-[5-(2H-pyrazol-3-yl)-pyridin-2-yloxy]-quinolin-3-ylmethyl}-piperidin-4-yl)-acetamide |

TABLE 1-continued

Examples of compounds of the invention.

| Ex. | Structure | Compound Name |
|---|---|---|
| 16 | 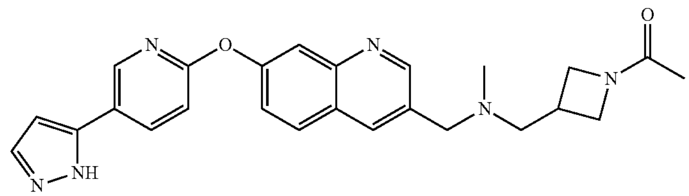 [SMILES: CC(=O)N1CC(CN(C)Cc2cnc3cc(Oc4ccc(-c5ccn[nH]5)cn4)ccc3c2)C1] | 1-{3-[(Methyl-{7-[5-(2H-pyrazol-3-yl)-pyridin-2-yloxy]-quinolin-3-ylmethyl}-amino)-methyl]-azetidin-1-yl}-ethanone |
| 17 | 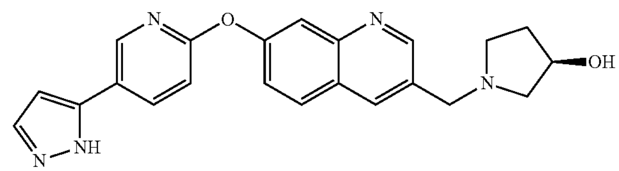 [SMILES: O[C@@H]1CCN(Cc2cnc3cc(Oc4ccc(-c5ccn[nH]5)cn4)ccc3c2)C1] | (R)-1-{7-[5-(2H-Pyrazol-3-yl)-pyridin-2-yloxy]-quinolin-3-ylmethyl}-pyrrolidin-3-ol |
| 18 | 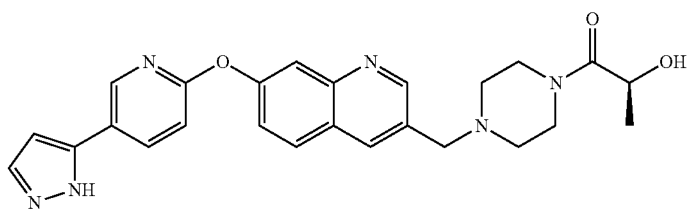 [SMILES: C[C@H](O)C(=O)N1CCN(Cc2cnc3cc(Oc4ccc(-c5ccn[nH]5)cn4)ccc3c2)CC1] | (S)-2-Hydroxy-1-(4-{7-[5-(2H-pyrazol-3-yl)-pyridin-2-yloxyl-quinolin-3-ylmethyl}-piperazin-1-yl)-propan-1-one |
| 19 | 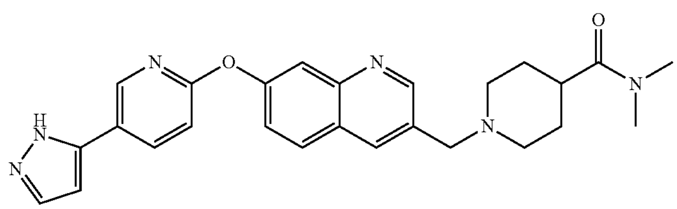 [SMILES: CN(C)C(=O)C1CCN(Cc2cnc3cc(Oc4ccc(-c5ccn[nH]5)cn4)ccc3c2)CC1] | 1-{7-[5-(2H-Pyrazol-3-yl)-pyridin-2-yloxy]-quinolin-3-ylmethyl}-piperidine-4-carboxylic acid dimethylamide |
| 20 | 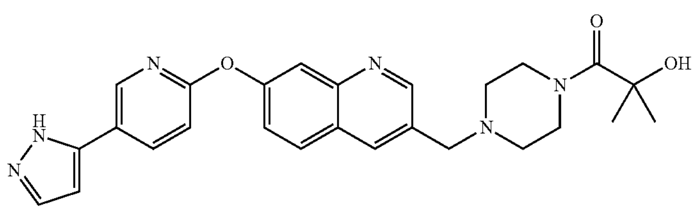 [SMILES: CC(C)(O)C(=O)N1CCN(Cc2cnc3cc(Oc4ccc(-c5ccn[nH]5)cn4)ccc3c2)CC1] | 2-Hydroxy-2-methyl-1-(4-{7-[5-(2H-pyrazol-3-yl)-pyridin-2-yloxy]-quinolin-3-ylmethyl)-piperazin-1-yl)-propan-1-one |
| 21 | 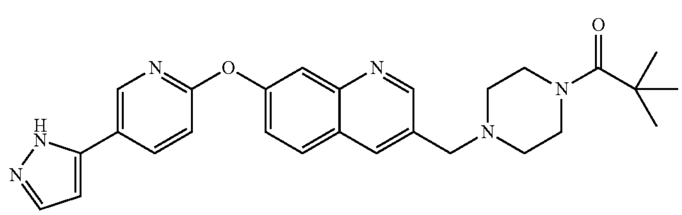 [SMILES: CC(C)(C)C(=O)N1CCN(Cc2cnc3cc(Oc4ccc(-c5ccn[nH]5)cn4)ccc3c2)CC1] | 2,2-Dimethyl-1-(4-{7-[5-(2H-pyrazol-3-yl)-pyridin-2-yloxy]-quinolin-3-ylmethyl}-piperazin-1-yl)-propan-1-one |
| 22 | 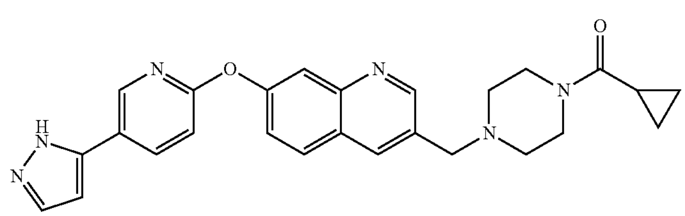 [SMILES: O=C(C1CC1)N1CCN(Cc2cnc3cc(Oc4ccc(-c5ccn[nH]5)cn4)ccc3c2)CC1] | Cyclopropyl-(4-{7-[5-(2H-pyrazol-3-yl)-pyridin-2-yloxy]-quinolin-3-ylmethyl}-piperazin-1-yl)-methanone |

| Ex. | Structure | Compound Name |
|---|---|---|
| 23 | 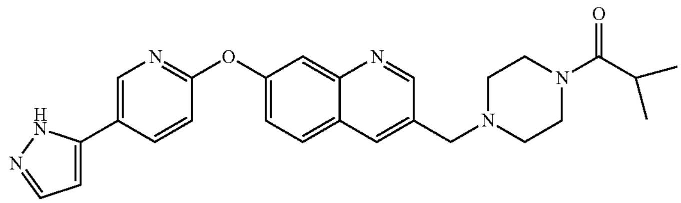 [SMILES: CC(C)C(=O)N1CCN(Cc2cnc3cc(Oc4ccc(-c5ccn[nH]5)cn4)ccc3c2)CC1] | 2-Methyl-1-(4-{7-[5-(2H-pyrazol-3-yl)-pyridin-2-yloxy-quinolin-3-ylmethyl}-piperazin-1-yl)-propan-1-one |

In a further embodiment, the invention relates to any one of the compounds depicted in Table 1, and pharmaceutically acceptable salts thereof.

In another embodiment, the invention relates to a compound selected from the group consisting of:
2-Hydroxy-1-(4-{7-[5-(2H-pyrazol-3-yl)-pyridin-2-yloxy]-quinolin-3-ylmethyl}-piperazin-1-yl)-ethanone;
1-(4-{7-[5-(2H-Pyrazol-3-yl)-pyridin-2-yloxy]-quinolin-3-ylmethyl}-piperazin-1-yl)-ethanone; 1-{7-[5-(2H-Pyrazol-3-yl)-pyridin-2-yloxy]-quinolin-3-ylmethyl}-azetidin-3-ol
2-Methoxy-1-(4-{7-[5-(2H-pyrazol-3-yl)-pyridin-2-yloxy]-quinolin-3-ylmethyl}-piperazin-1-yl)-ethanone;
(S)-3-Hydroxy-1-(1-{7-[5-(2H-pyrazol-3-yl)-pyridin-2-yloxy]-quinolin-3-ylmethyl}-piperidin-4-yl)-pyrrolidin-2-one;
3-(1-{7-[5-(2H-Pyrazol-3-yl)-pyridin-2-yloxy]-quinolin-3-ylmethyl}-piperidin-4-yl)-oxazolidin-2-one;
1-{7-[5-(2H-Pyrazol-3-yl)-pyridin-2-yloxy]-quinolin-3-ylmethyl}-piperidin-4-ol;
3-Methyl-1-{7-[5-(2H-pyrazol-3-yl)-pyridin-2-yloxy]-quinolin-3-ylmethyl}-azetidin-3-ol;
2-Hydroxy-1-[(R)-3-(methyl-{7-[5-(2H-pyrazol-3-yl)-pyridin-2-yloxy]-quinolin-3-ylmethyl}-amino)-pyrrolidin-1-yl]-ethanone; and
2-Hydroxy-1-[(S)-3-(methyl-{7-[5-(2H-pyrazol-3-yl)-pyridin-2-yloxy]-quinolin-3-ylmethyl}-amino)-pyrrolidin-1-yl]-ethanone;
and pharmaceutically acceptable salts thereof.

In another embodiment, the invention relates to a compound selected from the group consisting of:
2-Hydroxy-N-methyl-N—((S)-1-{7-[5-(2H-pyrazol-3-yl)-pyridin-2-yloxy]-quinolin-3-ylmethyl}-pyrrolidin-3-yl)-acetamide;
2-Hydroxy-N-methyl-N—((R)-1-{7-[5-(2H-pyrazol-3-yl)-pyridin-2-yloxy]-quinolin-3-ylmethyl}-pyrrolidin-3-yl)-acetamide;
(S)-1-{7-[5-(2H-Pyrazol-3-yl)-pyridin-2-yloxy]-quinolin-3-ylmethyl}-pyrrolidin-3-ol;
1-(4-{7-[5-(2H-Pyrazol-3-yl)-pyridin-2-yloxy]-quinolin-3-ylmethyl}-piperazin-1-yl)-propan-1-one;
2-Hydroxy-N-methyl-N-(1-{7-[5-(2H-pyrazol-3-yl)-pyridin-2-yloxy]-quinolin-3-ylmethyl}-piperidin-4-yl)-acetamide;
1-{3-[(Methyl-{7-[5-(2H-pyrazol-3-yl)-pyridin-2-yloxy]-quinolin-3-ylmethyl}-amino)-methyl]-azetidin-1-yl}-ethanone;
(R)-1-{7-[5-(2H-Pyrazol-3-yl)-pyridin-2-yloxy]-quinolin-3-ylmethyl}-pyrrolidin-3-ol;
(S)-2-Hydroxy-1-(4-{7-[5-(2H-pyrazol-3-yl)-pyridin-2-yloxy]-quinolin-3-ylmethyl}-piperazin-1-yl)-propan-1-one;
1-{7-[5-(2H-Pyrazol-3-yl)-pyridin-2-yloxy]-quinolin-3-ylmethyl}-piperidine-4-carboxylic acid dimethylamide;
2-Hydroxy-2-methyl-1-(4-{7-[5-(2H-pyrazol-3-yl)-pyridin-2-yloxy]-quinolin-3-ylmethyl}-piperazin-1-yl)-propan-1-one;
2,2-Dimethyl-1-(4-{7-[5-(2H-pyrazol-3-yl)-pyridin-2-yloxy]-quinolin-3-ylmethyl}-piperazin-1-yl)-propan-1-one;
Cyclopropyl-(4-{7-[5-(2H-pyrazol-3-yl)-pyridin-2-yloxy]-quinolin-3-ylmethyl}-piperazin-1-yl)-methanone; and
2-Methyl-1-(4-{7-[5-(2H-pyrazol-3-yl)-pyridin-2-yloxy]-quinolin-3-ylmethyl}-piperazin-1-yl)-propan-1-one;
and pharmaceutically acceptable salts thereof.

All terms as used herein in this specification, unless otherwise stated, shall be understood in their ordinary meaning as known in the art. Other more specific definitions are as follows:

Unless otherwise defined, the phrases "compound of formula (I)," "compounds of formula (I)," "compound of the invention" and "compounds of the invention" refer to the compounds described in any one of the embodiments above.

The term "$(C_1-C_6)$alkyl" refers to branched and unbranched alkyl groups having from 1 to 6 carbon atoms. Examples of —$(C_1-C_6)$alkyls include methyl, ethyl, n-propyl, isopropyl, n-butyl, sec-butyl, isobutyl, tert-butyl, n-pentane, iso-pentyl, neopentyl, n-hexane, iso-hexanes (e.g., 2-methylpentyl, 3-methylpentyl, 2,3-dimethylbutyl, and 2,2-dimethylbutyl). It will be understood that any chemically feasible carbon atom of the $(C_1-C_6)$alkyl group can be the point of attachment to another group or moiety.

The term "$(C_1-C_6)$alkylene" refers to branched and unbranched alkylene groups having from 1 to 6 carbon atoms. The $(C_1-C_6)$alkylenes include the $(C_1-C_6)$alkyl groups defined above except that a hydrogen atom of the $(C_1-C_6)$ alkyl is replaced with an group R (which R group may include another hydrogen). Non-limiting examples of $(C_1-C_6)$alkylenes include methylene, ethylene, propylene, butylene, pentylene, and hexylene. It will be understood that any chemically feasible carbon atom of the $(C_1-C_6)$alkylene group can be the point of attachment to another group or moiety.

The term "$(C_3-C_6)$cycloalkyl" refers to a nonaromatic 3- to 6-membered monocyclic carbocyclic radical. Examples of "$(C_3-C_6)$cycloalkyls" include cyclopropyl, cyclobutyl, cyclohexyl, cyclopentyl and cyclohexyl.

As used herein, the term "4- to 9-membered N-heterocycle" includes stable nonaromatic 4- to 7-membered monocyclic heterocyclic radicals containing one N atom and optionally containing 1-3 additional heteroatoms independently selected from N, O and S; stable nonaromatic 7- to 9-membered bridged heterobicyclic radicals containing one N atom and optionally containing 1-3 additional heteroatoms independently selected from N, O and S; and aromatic 6-membered heteroaryl radicals containing 1-3 N atoms. Thus, the 4- to 9-membered N-heterocycle consists of carbon atoms, at least one nitrogen atom, and optionally one to three additional hetero-ring atoms selected from nitrogen, oxygen and sulfur. It will be understood that when a 4- to 9-membered N-heterocycle contains a S ring atom, such S ring atom can be present in the ring in its divalent, tetravalent, or hexavalent form, i.e., —S—, —S(O)— or —S(O)$_2$—. The term 4- to 9-membered N-heterocycle also includes compounds in which the substituents on two adjacent ring atoms join to form a 4- to 6-membered fused ring, and/or the substituents on the same ring atom join to form a 4- to 6-membered spirocyclic ring. It will be understood that any 4- to 6-membered fused ring or 4- to 6-membered spirocyclic ring may contain one to three additional ring hetero atoms selected from nitrogen, oxygen and sulfur, and said fused and spirocyclic rings may be further substituted. The heterocycle may be either saturated or partially unsaturated. Non-limiting examples of stable nonaromatic 4- to 7-membered monocyclic heterocyclic radicals include azetidinyl, pyrrolidinyl, piperazinyl, piperidinyl, morpholinyl, thiomorpholinyl, azepanyl, 1,4-diazepanyl and 1,4-oxazepanyl. Non-limiting examples of stable nonaromatic 4- to 7-membered monocyclic heterocyclic radicals having a spirocyclic group include 2-oxa-6-aza-spiro[3.4]octane, 1,8-diaza-spiro[4.5]decan-2-one, 2-oxa-6-aza-spiro[3.5]nonane, 1,8-diaza-spiro[4.5]decane, and 2-oxa-6-aza-spiro[3.3]heptane. Non-limiting examples of stable nonaromatic 4- to 7-membered monocyclic heterocyclic radicals fused to a 4- to 6-membered-ring include hexahydro-oxazolo[3,4-a]pyrazin-3-one, hexahydro-pyrrolo[1,2-a]pyrazin-6-one, and octahydro-pyrrolo[3,4-c]pyrrole. Non-limiting examples of stable nonaromatic 7 to 9-membered bridged N-heterobicyclic radicals include 2-thia-5-aza-bicyclo[2.2.1]heptane 2,2-dioxide, 3,8-diaza-bicyclo[3.2.1]octane, 8-oxa-3-aza-bicyclo[3.2.1]octane, 8-aza-bicyclo[3.2.1]octane, 2,5-diaza-bicyclo[2.2.1]heptane, 2,5-diaza-bicyclo[2.2.2]octane, and 2-oxa-5-aza-bicyclo[2.2.1]heptane. Non-limiting examples of aromatic 6-membered heteroaryl radicals include pyridine and pyrimidine.

As used herein, the term "4- to 7-membered heterocycle" refers to stable nonaromatic 4- to 7-membered monocyclic heterocyclic radicals and stable aromatic 5- to 6-membered monocyclic heterocyclic radicals (or "5 to 6-membered heteroaryl"). The 4- to 7-membered heterocycle consists of carbon atoms and one or more, preferably from one to four heteroatoms chosen from nitrogen, oxygen and sulfur. The nonaromatic 4- to 7-membered monocyclic heterocyclic may be either saturated, partially unsaturated, or aromatic. Non-limiting examples of nonaromatic 4- to 7 membered monocyclic heterocyclic radicals include tetrahydrofuranyl, azetidinyl, oxazolidinyl tetrahydropyrrolidinyl, pyranyl, tetrahydropyranyl, dioxanyl, thiomorpholinyl, thiomorpholinyl, morpholinyl, piperidinyl, piperazinyl, 1,3-oxazinanyl and azepinyl. The 5- to 6-membered heteroaryl consists of carbon atoms and one or more, preferably from one to three heteroatoms chosen from nitrogen, oxygen and sulfur. Non-limiting examples of 5 to 6-membered monocyclic heteroaryl rings include furanyl, oxazolyl, isoxazolyl, oxadiazolyl, pyranyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. It will be understood that when a 4- to 7-membered heterocycle contains a S ring atom, such S ring atom can be present in the ring in its divalent, tetravalent, or hexavalent form, i.e., —S—, —S(O)— or —S(O)$_2$—.

Each aryl or heteroaryl unless otherwise specified includes it's partially or fully hydrogenated derivatives. For example, quinolinyl may include decahydroquinolinyl and tetrahydroquinolinyl, naphthyl may include its hydrogenated derivatives such as tetrahydronaphthyl. Other partially or fully hydrogenated derivatives of the aryl and heteroaryl compounds described herein will be apparent to one of ordinary skill in the art.

The term "heteroatom" as used herein shall be understood to mean atoms other than carbon such as O, N, and S.

The term "halo" or "halogen" refers to fluoro, chloro, bromo or iodo.

The symbol

means point of attachment of a group R to a moiety.

In all alkyl groups or carbon chains one or more carbon atoms can be optionally replaced by heteroatoms: O, S or N. It shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The invention also relates to pharmaceutical preparations, containing as active substance one or more compounds of the invention, or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g. $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms which may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Where compounds of the invention can exist in more than one tautomeric form, the invention includes methods using all such tautomers.

The compounds of the invention are only those which are contemplated to be "chemically stable" as will be appreciated by those skilled in the art. For example, a compound which would have a "dangling valency", or a "carbanion" is not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a to pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the invention.

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and $N—(C_1-C_4)alkyl)^{4+}$ salts.

In addition, within the scope of the invention is use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

General Synthetic Methods

The compounds of the invention may be prepared by the examples presented below, and methods known to those of ordinary skill in the art and reported in the chemical literature. Optimum reaction conditions and reaction times may vary depending on the particular reactants used. Unless otherwise specified, solvents, temperatures, pressures and other reaction conditions may be readily selected by one of ordinary skill in the art. Specific procedures are provided in the Synthetic Examples section.

All synthetic intermediates described in this application such as the amine intermediates disclosed in the embodiments of the invention as groups of formula —$N(R^2)(R^3)$, or 4- to 9-membered N-heterocyclic ring are either commercially available, are prepared according to the described synthesis procedures, or may be prepared by one skilled in the art using methods described in the chemical literature.

Amide bond formation reactions utilized for the preparation of the intermediates of this invention may be carried out by standard coupling conditions well-known in the art (e.g., Bodanszky, M. *The Practice of Peptide Synthesis*, Springer-Verlag, 1984, which is hereby incorporated by reference in its entirety), such as reacting a carboxylic acid and an amine in the presence of 1-(3-dimethylaminopropyl)-3-ethylcarbodiimide (EDC) and 1-hydroxybenzotriazole.

The methods described below, in the "Synthesis of Intermediate" section, and in the "Syntheses of Compounds of Formula I" section may be used to prepare compounds of formula I. In the schemes below, R groups (e.g., $R^1$, $R^2$, and $R^3$) shall have the meanings defined in the detailed description of compounds of formula I, and PG shall be protecting group such as trimethylsilanyl-ethoxymethyl (SEM).

Compounds of formula I may be prepared according to Schemes I-II.

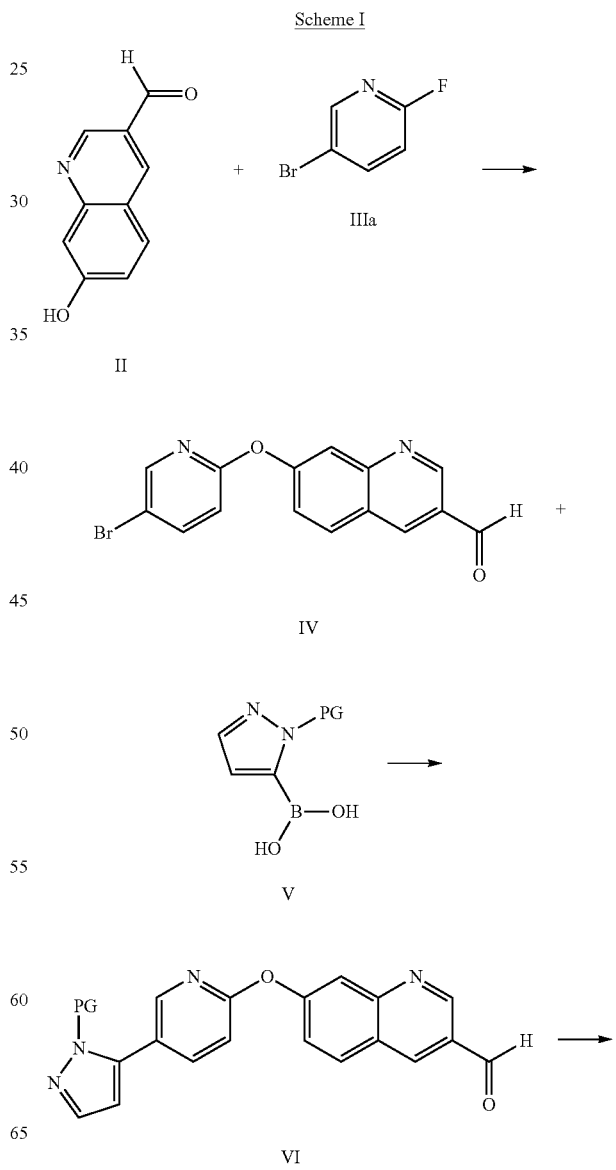

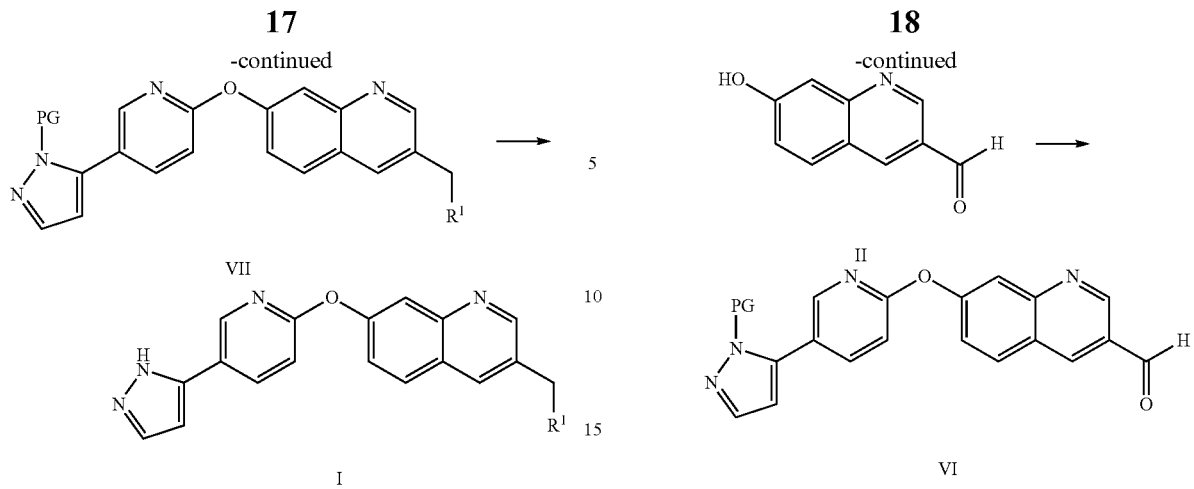

As illustrated in Scheme I, 7-hydroxy-3-quinolinecarboxaldehyde of the formula II may be reacted with 5-bromo-2-fluoro-pyridine IIIa in the presence of a suitable base such as $Cs_2CO_3$ in a suitable solvent such as DMF, and at a suitable temperature such as 140° C. to provide the quinoline of formula IV. Compound of formula IV may be heated at a suitable temperature such as 100° C. with a suitably protected (e.g., SEM-protected) 1H-pyrazol-3-yl boronic acid of formula V in the presence of suitable cross coupling reagents such as a Pd catalyst (e.g., $Pd(PPh_3)_4$), a base (e.g., $Na_2CO_3$), and a mixture of degassed solvents (e.g., a mixture of EtOH and toluene), under an inert atmosphere (e.g., argon) to afford the aldehyde of formula VI. Compound of formula VI may be reacted with a suitable amine reagent $R^1$ such as an amine of formula $—N(R^2)(R^3)$, or a 4- to 9-membered N-heterocyclic amine in the presence of a suitable hydride reagent such as sodiumtriacetoxyborohydride in a suitable solvent such as DCM and at a suitable temperature such as the ambient temperature to furnish the compound of formula VII. Compound of formula VII may be deprotected using a suitable reagent (e.g., TFA reagent for SEM deprotection) in a suitable solvent such as DCM at a suitable temperature such as the ambient temperature to give the compound of formula I.

Alternatively, compound of formula VI may be synthesized according to the general procedure shown in Scheme II.

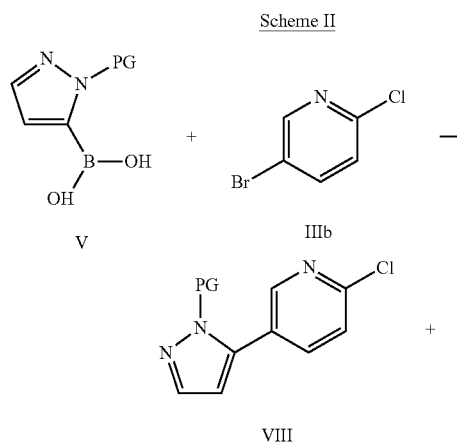

Scheme II

As illustrated in Scheme II, a compound of formula IIIb may be heated at a suitable temperature (e.g., 76° C.) with a suitably protected (e.g., SEM-protected) 1H-pyrazol-3-yl boronic acid of formula V in the presence of suitable cross coupling reagents such as a Pd catalyst (e.g., $Pd(PPh_3)_4$), a base (e.g., $Na_2CO_3$), and a mixture of degassed solvents (e.g., a mixture of water and THF), under an inert atmosphere (e.g., argon) to afford the chloropyridine of formula VIII. Compound of formula VIII may be reacted with 7-hydroxy-3-quinolinecarboxaldehyde of the formula II in the presence of a suitable base such as $K_2CO_3$ in a suitable solvent such as DMF, and at a suitable temperature such as 120° C. to give the aldehyde of formula VI. Compound of formula VI may be converted to the compound of formula I according to the general experimental procedure described in Scheme I.

EXAMPLES

General Methods

Unless noted otherwise, all reactions are run at ambient temperature (about 25° C.), under inert atmosphere (e.g., Argon, $N_2$), and under anhydrous conditions. All compounds are characterized by at least one of the following methods: $^1H$ NMR, HPLC, HPLC-MS, and melting point.

Typically, reaction progress is monitored by thin layer chromatography (TLC) or HPLC-MS. Intermediates and products are purified using at least one of the following methods:

Flash chromatography on silica gel,
Recrystallization,
Chiral HPLC using a 20×500 mm Chiralpak AD-H column, or 20×500 mm
Chiralpak OD-H column, and eluting with an isocratic mixture of isopropanol in heptanes with 0.1% diethylamine (DEA) at 7.5 mL/min,
20×250 mm Chiralcel OD-H column, and eluting with an isocratic mixture of isopropanol in heptanes at 7.5 mL/min,
Super Critical Fluid (SCF) Chiral HPLC using a 3.0×25.0 cm RegisPack column, eluting with an isocratic mixture of MeOH, isopropylamine (IPA), and super critical carbon dioxide at 125 bar; 80 mL/min, and/or
Reversed phase HPLC using a C18 semi-preparative column eluting with a gradient of MeCN+0.1% TFA/$H_2O$+ 0.1% TFA, or MeCN+0.1% formic acid/$H_2O$+0.1% formic acid.

The reported MS data is for observed [M+H]⁺. For bromine containing compounds, the [M+H]⁺ is either reported for one or both of the bromine isotopes (i.e., $^{79}$Br and $^{81}$Br).

Compounds of the invention are characterized using LC/MS/MS with electron spray ionization (ESI). The LC method includes the following parameters:

Injection volume: 5 uL

Mobile Phases: 0.1% Formic Acid in Water (A) and 0.1% Formic Acid in Acetonitrile (B) (HPLC grade)

Left and Right Temperature: 35° C.

Run Time: 4 min

Column: Thermo Scientific, Aquasil C18, 50×2.1 mm, 5µ, part number 77505-052130, or equivalent LC Pump Gradient:

| Total Time (min) | Flow Rate (uL/min) | % A | % B |
|---|---|---|---|
| 0 | 500 | 90.0 | 10.0 |
| 0.5 | 500 | 90.0 | 10.0 |
| 1.5 | 500 | 1.0 | 99.0 |
| 2.5 | 500 | 1.0 | 99.0 |
| 3.0 | 500 | 90.0 | 10.0 |
| 4.0 | 500 | 90.0 | 10.0 |

Synthesis of Intermediates

Intermediate A: Preparation of 7-{5-[2-(2-Trimethyl-silanyl-ethoxymethyl)-2H-pyrazol-3-yl]-pyridin-2-yloxy}-quinoline-3-carbaldehyde (A)

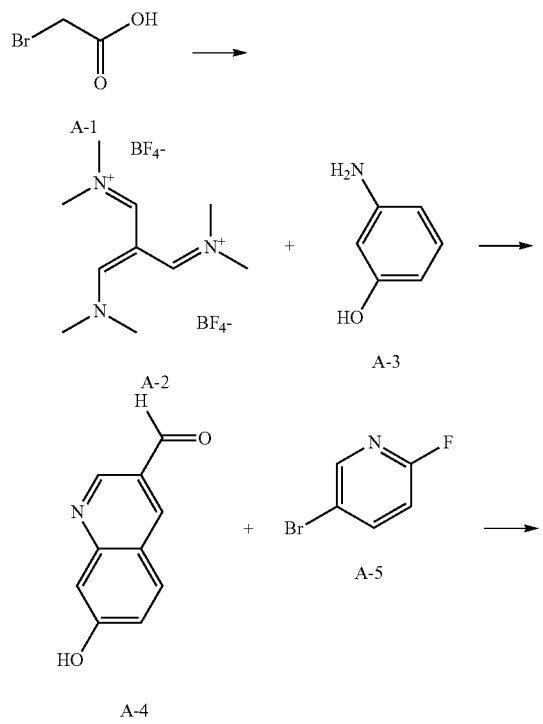

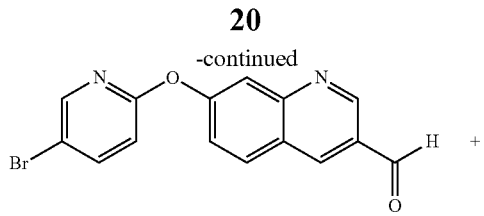

A-6

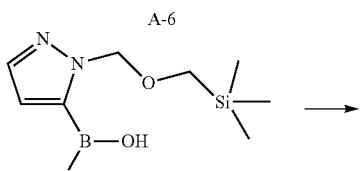

A-7

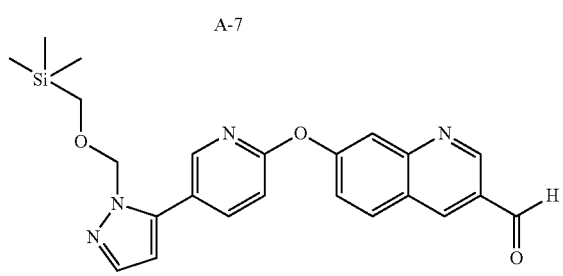

A

To a stirred solution of A-1 (500 g, 3.59 mol) in POCl₃ (1.00 L, 10.8 mol) is added DMF (1.63 L, 21.9 mol) slowly at 0° C. for a period of 2 h. The reaction mixture is slowly heated to 65° C. and stirred for 15 min. The reaction temperature is raised to 120° C. and the mixture is stirred for 3 h. The mixture is slowly cooled to 0° C. Methanol (2.0 L) and 48% tetrafluoroboric acid in water (1.31 L, 7.19 mol) is added to the mixture over 30-40 min Isopropyl alcohol (2.0 L) is added to the mixture at 0° C. and the resultant mixture is stirred at 0° C. for 2 h while the reaction progress is monitored by TLC. Upon completion, the crude product (A-2) in 7 L of solvent is directly taken to the next step without purification.

The solution of A-2 from the previous step (approximately 800 g, 2.96 mol) is added drop-wise at ambient temperature to a stirred solution of A-3 (216 g, 1.97 mol) in MeOH (5.0 L). The reaction mixture is heated to 80° C. for 7 h, cooled to ambient temperature and concentrated. The residue is dissolved in water and basified with solid NaHCO₃ to pH 7-8.

The resultant precipitate is filtered, washed with water, and dried under vacuum to give A-4.

To a stirred solution of A-4 (500.0 g, 2.88 mol) and A-5 (407 g, 2.30 mol) in DMF (5 L) is added Cs₂CO₃ (1,125 g, 3.45 mol) over 30 min at ambient temperature under N₂ atmosphere. The reaction mixture is heated at 140° C. for 6 h, cooled to ambient temperature and diluted with ice cold water. The mixture is extracted with EtOAc (2×3 L). The combined organic layers are washed with water and brine. Organic layer is dried over anhydrous Na₂SO₄ and concentrated under vacuum. The crude product is purified by silica gel column chromatography eluting with 30% EtOAc in petroleum ether to afford A-6.

To a stirred solution of A-6 (100 g, 304 mmol) and A-7 (142 g, 607 mmol) in a mixture of EtOH (1.6 L) and toluene (4.0 L) is added Na$_2$CO$_3$ (79.5 g, 750 mmol). The reaction mixture is purged with argon for 1 h, Pd(PPh$_3$)$_4$ (34.6 g, 29.9 mmol) is added, the resultant mixture is purged with argon for an additional 30 min, and heated at 100° C. overnight. The reaction mixture is cooled to ambient temperature, filtered through diatomaceous earth, and the filter pad is washed with EtOH. The filtrate is concentrated under vacuum, diluted with water and extracted with EtOAc (2×1.5 L). The combined organic layers are washed with water and brine, dried over anhydrous Na$_2$SO$_4$, filtered and concentrated. The residue is triturated with petroleum ether and filtered. The resultant solid is dried under vacuum to afford the title product (A).

Intermediate B: Preparation of
2-Hydroxy-1-piperazin-1-yl-ethanone (B)

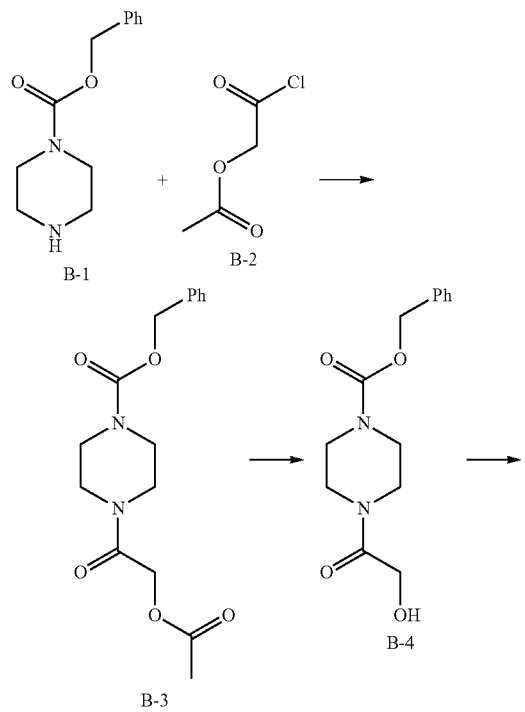

-continued

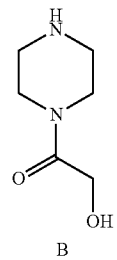

B

B-2 (15.0 g, 110 mmol) is added drop-wise to a mixture of B-1 (24.2 g, 110 mmol) and triethyl amine (31.7 mL, 220 mmol) in MeCN (300 mL) at 0° C. The resultant mixture is stirred for 30 minutes at ambient temperature, poured into ice water, and extracted with EtOAc (200 mL). The organic layer is washed with saturated aqueous NaHCO$_3$ and brine, dried over Na$_2$SO$_4$, filtered and concentrated to afford B-3, which is used in the next step without purification.

To a solution of B-3 (34.0 g, 106 mmol) in a mixture of dioxane (100 mL) and water (50 mL) is added LiOH.H$_2$O (11.1 g, 265 mmol). The mixture is stirred ambient temperature to for 2 h, neutralized with concentrated HCl, and extracted with EtOAc (2×100 mL). The combined organic layer are dried over anhydrous Na$_2$SO$_4$, filtered and concentrated. The crude product is purified in SiO$_2$ (eluting with 0-75% EtOAc in DCM) to give B-4. To a solution of B-4 (21.5 g, 77.3 mmol) in absolute EtOH (250 mL) is added 10% Pd/C (8.22 g). The reaction mixture is evacuated and charged with H$_2$, and stirred under a balloon of H$_2$ overnight. After 24 h, the mixture is evacuated and purged with argon, and filtered through a pad of diatomaceous earth. The filter pad is washed with EtOH, and the filtrate is concentrated to afford the title product (B).

The following intermediates are synthesized from intermediate B-1 and their corresponding acyl chloride reagents according to the procedure described for the synthesis of intermediate B.

| Intermediate | Structure | Intermediate Name | Acyl Chloride |
|---|---|---|---|
| C | 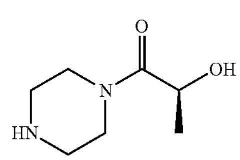 | (S)-2-Hydroxy-1-piperazin-1-yl-propan-1-one | |
| D | 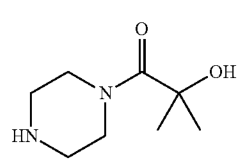 | 2-Hydroxy-2-methyl-1-piperazin-1-yl-propan-1-one | |

Intermediate E: Preparation of 2-methoxy-1-piperazin-1-yl-ethanone (E)

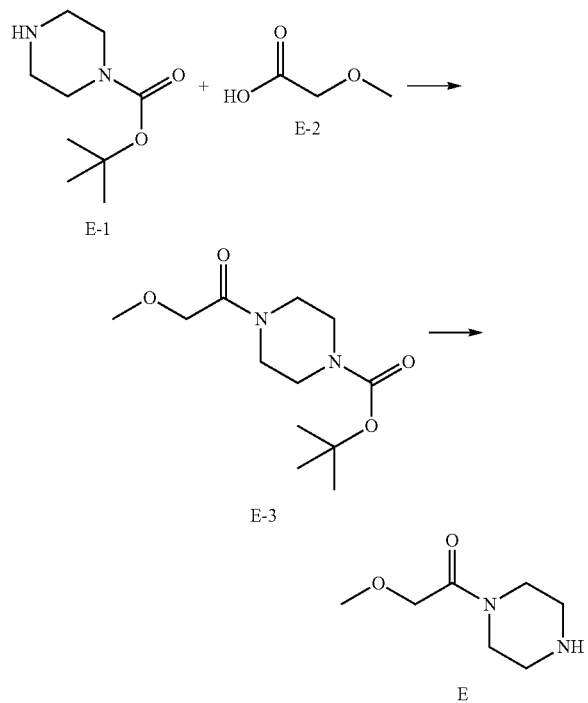

A stirred solution of E-2 (100 mL, 1.25 mmol) in MeCN (10 mL) is treated with TBTU (400 mg, 1.25 mmol). After 20 minutes, E-1 (0.190 g, 1.00 mmol) is added and the mixture is stirred overnight. The reaction is poured into dilute aqueous $Na_2CO_3$, and extracted with DCM (3×5 mL). The combined extracts are dried over $Na_2SO_4$, filtered and concentrated. The residue is dissolved in DCM and passed through a MP-TSOH cartridge, and concentrated to afford E-3.

A stirred solution of E-3 (0.100 g, 0.380 mmol) in 1,4-dioxane (4 mL) is treated with a solution of HCl in 1,4-dioxane (4M, 1 mL). After 72 h, the reaction is concentrated, redissolved in wet MeOH, passed through a PL-$HCO_3$ cartridge, and concentrated to afford the title product (E).

Intermediate F: Preparation of Acetic acid (methyl-piperidin-4-yl-carbamoyl)-methyl ester.TFA (F)

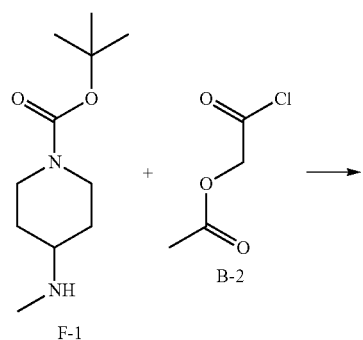

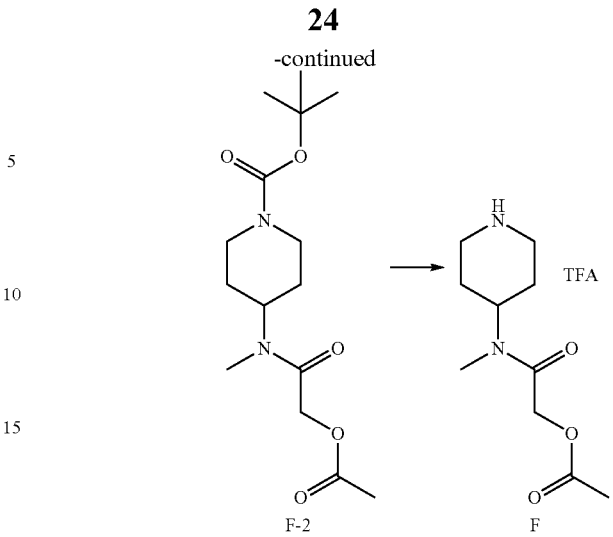

Intermediate F-2 is prepared from intermediates F-1 (1.00 g, 4.66 mmol) and B-2 (637 mg, 4.66 mmol) according to the procedure described for the synthesis of intermediate B-3. To intermediate F-2 (1.30 g, 4.14 mmol) is added a solution of TFA/DCM (6 mL, 1:1). The mixture is stirred at ambient temperature for 2 h and concentrated to give the crude title product (F), which was used in the next step without purification.

Intermediate G: Preparation of Acetic acid ((R)-methyl-pyrrolidin-3-yl-carbamoyl)-methyl ester (G)

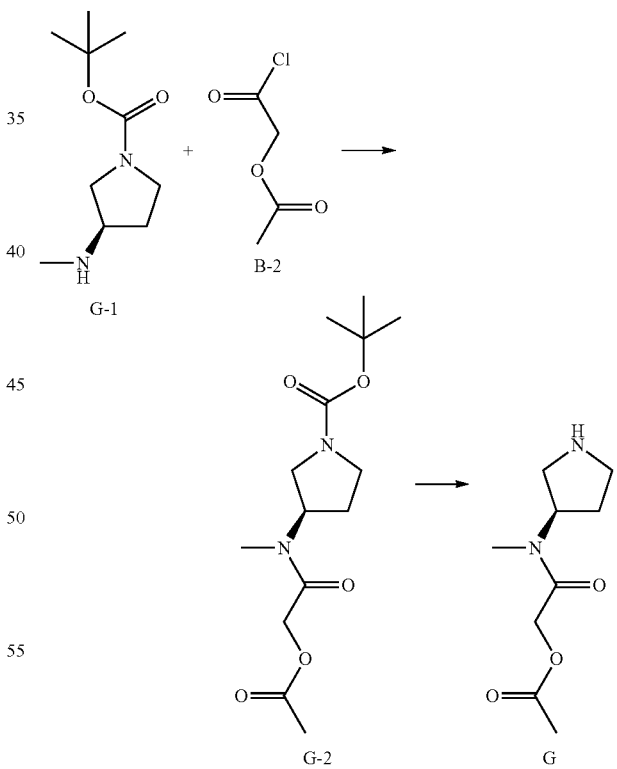

To a solution of G-1 (1.00 g, 4.84 mmol) in DCM (5 mL) at −35° C. is added DIPEA (2.61 mL, 14.5 mmol) followed by B-2 (644 mL, 5.81 mmol). The reaction is warmed up to ambient temperature over 1 h and stirred for 24 h. The mixture is diluted with EtOAc (125 mL), and washed with saturated aqueous $NH_4Cl$ (100 mL), saturated aqueous $NaHCO_3$ (100 mL) and brine (40 mL). The combined aqueous layers are extracted with EtOAc (125 mL). The organic layers are pooled, dried over Na₂SO₄, filtered and concentrated to afford G-2, which is used in the next step without purification.

To a solution of G-2 (1.53 g, 4.84 mmol) in DCM (50 mL) is added HCl in 1,4-dioxane (24.7 mL, 4 M, 98.8 mmol) at ambient temperature. The mixture is stirred at ambient temperature for 24 h, concentrated in vacuo, dissolved in a mixture of MeOH and DCM (1 mL: 100 mL), treated with PS-DIEA resin (3.5 g) and stirred for 18 h. The suspension is filtered, and the filtrate is concentrated to afford the title product (G), which is used in the next step without purification.

The following intermediates are synthesized from their corresponding starting material and B-2 according to the procedure described for the synthesis of intermediate G.

-continued

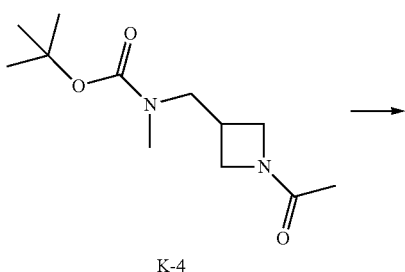

K-4

| Intermediate | Structure | Intermediate Name | Starting Material |
|---|---|---|---|
| H | 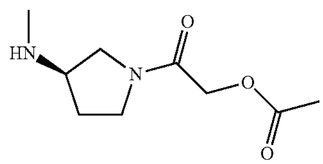 | Acetic acid 2-((R)-3-methylamino-pyrrolidin-1-yl)-2-oxo-ethyl ester | |
| I | 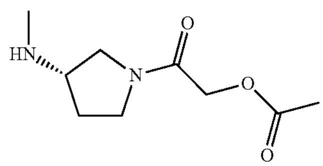 | Acetic acid 2-((S)-3-methylamino-pyrrolidin-1-yl)-2-oxo-ethyl ester | |
| J | 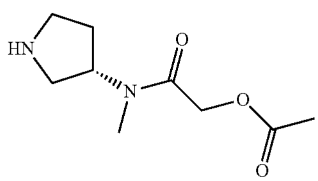 | Acetic acid ((S)-methyl-pyrrolidin-3-yl-carbamoyl)-methyl ester | |

Intermediate K: Preparation of 1-(3-Methylaminomethyl-azetidin-1-yl)-ethanone.HCl (K)

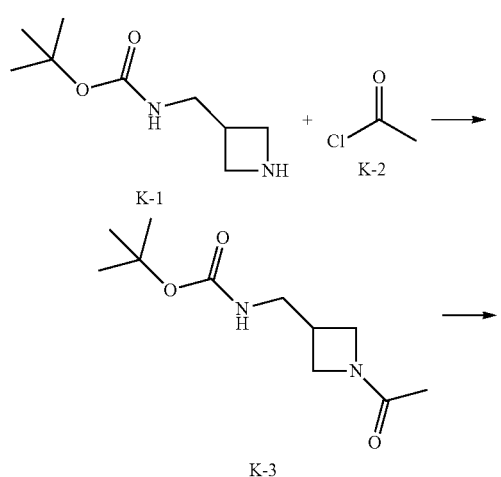

-continued

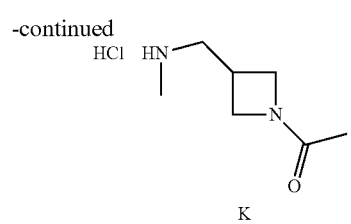

K

To a solution of K-1 (7.90 g, 40.9 mmol) and TEA (11.5 mL, 82.5 mmol) in DCM (125 mL) at −10° C. is added K-2 (3.2 mL, 44 mmol). The resultant mixture is warmed to ambient temperature, and stirred for 18 h. The reaction mixture is concentrated, and the residue is dissolved in EtOAc (300 mL). The organic layer is extracted with saturated aqueous NaHCO₃ (200 mL), saturated aqueous NH₄Cl (200 mL), and brine (50 mL), dried over Na₂SO₄, filtered and concentrated to afford K-3.

To a solution of K-3 (8.50 g, 36.1 mmol) in THF (100 mL) at 0° C. is added sodium hydride (60% dispersion in oil, 3.00 g, 75.0 mmol), and the resultant mixture is stirred for 1 h at 0° C. Iodomethane (4.6 mL, 75 mmol) is added, and the mixture is stirred at ambient temperature for 24 h. The reaction mixture is cooled to 0° C., quenched with saturated aqueous NH₄Cl (300 mL), and extracted with EtOAc (3×300 mL). The combined organic layers are washed with brine (50 mL), dried over Na$_2$SO$_4$, filtered and concentrated. The residue is purified by flash chromatography eluting with 0-5% MeOH in DCM to give K-4.

A stirred solution of K-4 (8.23 g, 32.9 mmol) in DCM (200 mL) is treated with a solution of HCl in 1,4-dioxane (4M, 82.3 mL). After 18 h, the reaction mixture is concentrated. The resultant residue is titrated with ether, and dried in vacuo under P$_2$O$_5$ to afford the title product (K).

Syntheses of Compounds of Formula I

Methods of making the compounds of the invention are described in detail below. Mass spectral data for the compounds of the invention are found in Table 2.

Example 1

Preparation of 2-Hydroxy-1-(4-{7-[5-(2H-pyrazol-3-yl)-pyridin-2-yloxy]-quinolin-3-ylmethyl}-piperazin-1-yl)-ethanone (1)

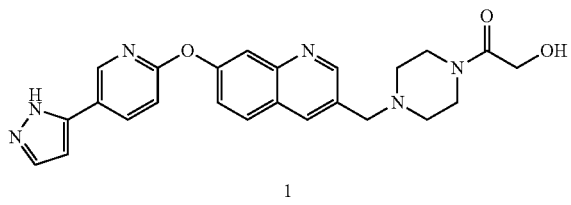

A stirred solution of intermediates A (44 mg, 0.099 mmol) and B (21.3 mg, 0.148 mmol) in DCM (2 mL) is treated with sodiumtriacetoxyborohydride (31.3 mg, 0.148 mmol). The resultant mixture is stirred at ambient temperature for 24 h. The reaction mixture is diluted with DCM and quenched with saturated aqueous NaHCO$_3$. Phases are separated. The organic layer is dried over Na$_2$SO$_4$, filtered and concentrated to give the crude 1-1, which is used in the next step without purification.

To intermediate 1-1 (56.9 mg) is added a solution of TFA/DCM (1 mL, 1:1). The mixture is stirred at ambient temperature for 2 h and concentrated. The residue is purified by reversed phase HPLC eluting with 0-50% MeCN in water (+0.1% TFA). Fractions containing the desired product are combined and concentrated. The residue is dissolved in DCM and washed with saturated aqueous NaHCO$_3$. The organic layer is dried over anhydrous Na$_2$SO$_4$, filtered and concentrated to afford the title product (1).

The title product (1) may also be prepared by the procedure described below

Alternative preparation of 2-Hydroxy-1-(4-{7-[5-(2H-pyrazol-3-yl)-pyridin-2-yloxy]-quinolin-3-ylmethyl}-piperazin-1-yl)-ethanone (1)

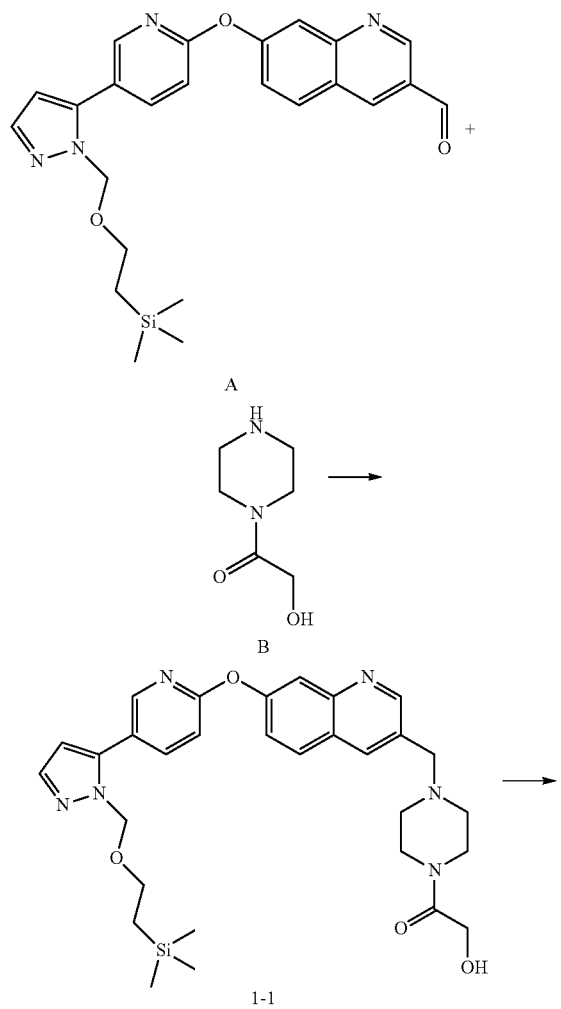

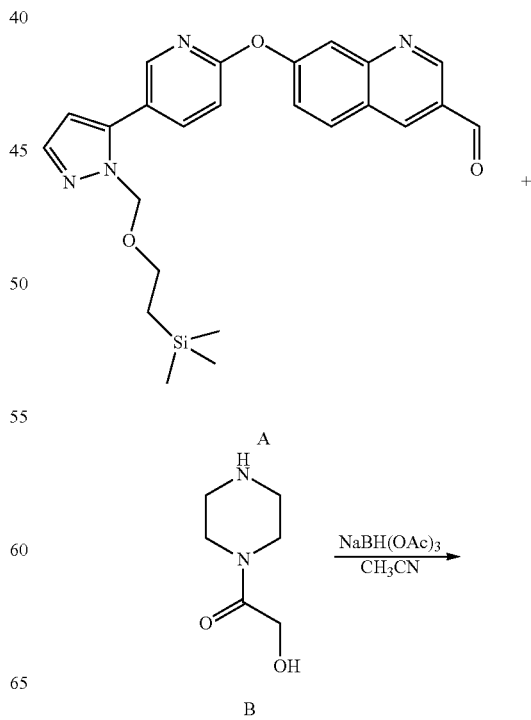

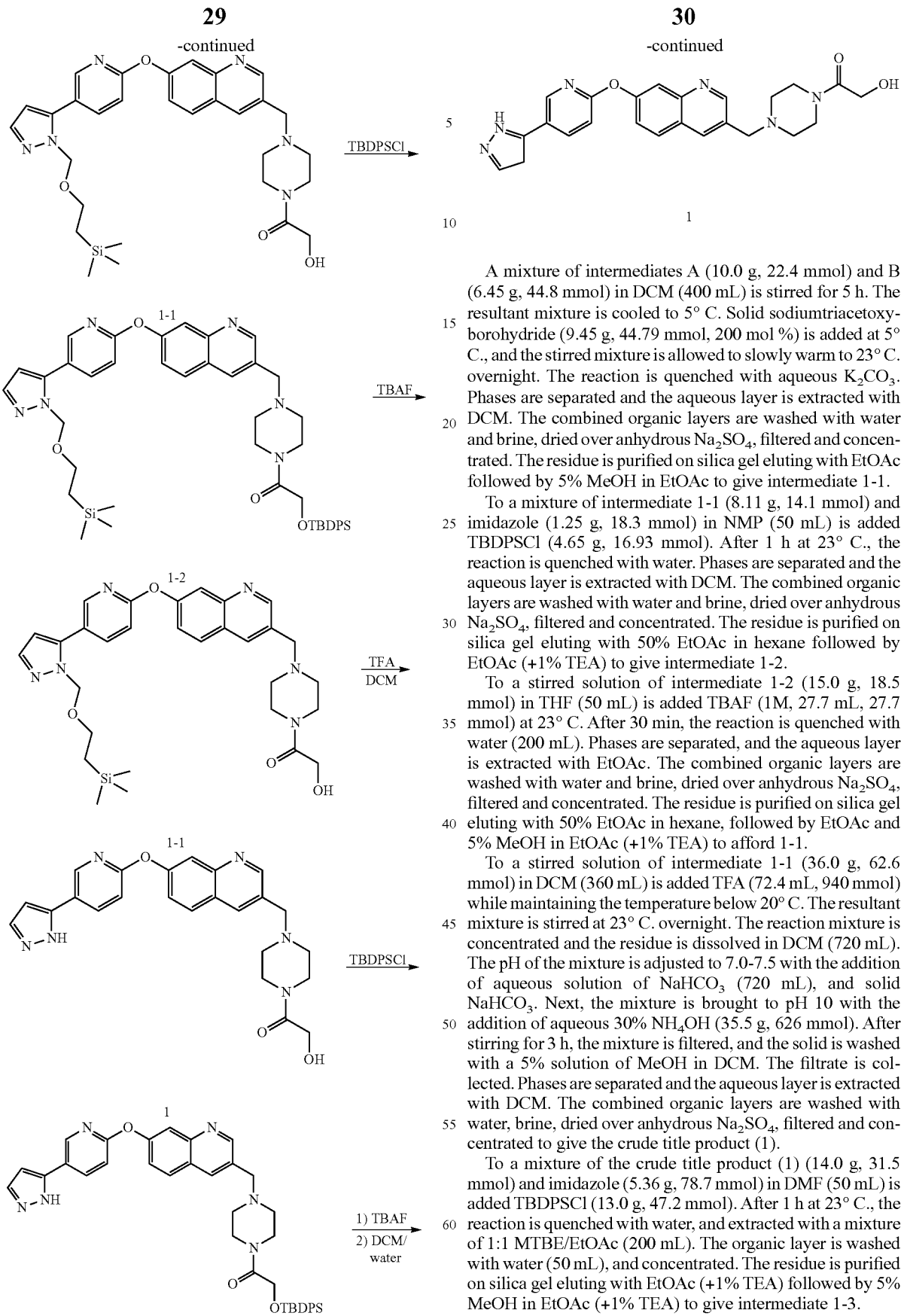

A mixture of intermediates A (10.0 g, 22.4 mmol) and B (6.45 g, 44.8 mmol) in DCM (400 mL) is stirred for 5 h. The resultant mixture is cooled to 5° C. Solid sodiumtriacetoxyborohydride (9.45 g, 44.79 mmol, 200 mol %) is added at 5° C., and the stirred mixture is allowed to slowly warm to 23° C. overnight. The reaction is quenched with aqueous $K_2CO_3$. Phases are separated and the aqueous layer is extracted with DCM. The combined organic layers are washed with water and brine, dried over anhydrous $Na_2SO_4$, filtered and concentrated. The residue is purified on silica gel eluting with EtOAc followed by 5% MeOH in EtOAc to give intermediate 1-1.

To a mixture of intermediate 1-1 (8.11 g, 14.1 mmol) and imidazole (1.25 g, 18.3 mmol) in NMP (50 mL) is added TBDPSCl (4.65 g, 16.93 mmol). After 1 h at 23° C., the reaction is quenched with water. Phases are separated and the aqueous layer is extracted with DCM. The combined organic layers are washed with water and brine, dried over anhydrous $Na_2SO_4$, filtered and concentrated. The residue is purified on silica gel eluting with 50% EtOAc in hexane followed by EtOAc (+1% TEA) to give intermediate 1-2.

To a stirred solution of intermediate 1-2 (15.0 g, 18.5 mmol) in THF (50 mL) is added TBAF (1M, 27.7 mL, 27.7 mmol) at 23° C. After 30 min, the reaction is quenched with water (200 mL). Phases are separated, and the aqueous layer is extracted with EtOAc. The combined organic layers are washed with water and brine, dried over anhydrous $Na_2SO_4$, filtered and concentrated. The residue is purified on silica gel eluting with 50% EtOAc in hexane, followed by EtOAc and 5% MeOH in EtOAc (+1% TEA) to afford 1-1.

To a stirred solution of intermediate 1-1 (36.0 g, 62.6 mmol) in DCM (360 mL) is added TFA (72.4 mL, 940 mmol) while maintaining the temperature below 20° C. The resultant mixture is stirred at 23° C. overnight. The reaction mixture is concentrated and the residue is dissolved in DCM (720 mL). The pH of the mixture is adjusted to 7.0-7.5 with the addition of aqueous solution of $NaHCO_3$ (720 mL), and solid $NaHCO_3$. Next, the mixture is brought to pH 10 with the addition of aqueous 30% $NH_4OH$ (35.5 g, 626 mmol). After stirring for 3 h, the mixture is filtered, and the solid is washed with a 5% solution of MeOH in DCM. The filtrate is collected. Phases are separated and the aqueous layer is extracted with DCM. The combined organic layers are washed with water, brine, dried over anhydrous $Na_2SO_4$, filtered and concentrated to give the crude title product (1).

To a mixture of the crude title product (1) (14.0 g, 31.5 mmol) and imidazole (5.36 g, 78.7 mmol) in DMF (50 mL) is added TBDPSCl (13.0 g, 47.2 mmol). After 1 h at 23° C., the reaction is quenched with water, and extracted with a mixture of 1:1 MTBE/EtOAc (200 mL). The organic layer is washed with water (50 mL), and concentrated. The residue is purified on silica gel eluting with EtOAc (+1% TEA) followed by 5% MeOH in EtOAc (+1% TEA) to give intermediate 1-3.

To a stirred solution of intermediate 1-3 (10.8 g, 15.7 mmol) in 2-MeTHF (45 mL) is added TBAF (7.84 mL, 7.84 mmol) at 10° C. The reaction is warmed to 23° C. and stirred for 30 min. To the mixture is added DCM (100 mL) and water (45 mL) at 23° C., and the stirring is continued for 1 h. The resultant solid is filtered and washed with a mixture of DCM (50 mL) and water (50 mL) to give the first crop of the title product (1). The filtrate is concentrated, re-dissolved in EtOAc (20 mL), and stirred for 5 h at 23° C. The resultant solid is filtered and washed with EtOAc (10 mL) to provide a second crop of the title product (1).

Example 2

Preparation of 1-(4-{7-[5-(2H-Pyrazol-3-yl)-pyridin-2-yloxy]-quinolin-3-ylmethyl}-piperazin-1-yl)-ethanone (2)

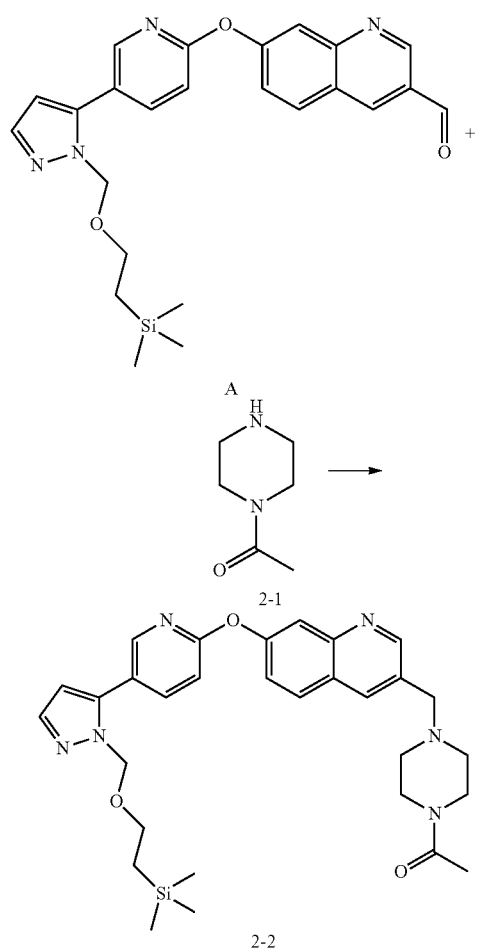

A stirred solution of intermediates A (3.00 g, 6.72 mmol) and 2-1 (3.44 g, 26.8 mmol) in DCM (100 mL) is treated with sodiumtriacetoxyborohydride (2.85 g, 13.4 mmol). The resultant mixture is stirred at ambient temperature for 24 h. The organic layer is quenched with saturated aqueous NaHCO₃. Phases are separated, and the organic layer is dried over Na₂SO₄, filtered and concentrated. The residue is purified by flash chromatography (eluting with 100% EtOAc followed by 0-7% MeOH in DCM) to give the intermediate 2-2. MS (ES+): m/z 559.8 [M+H]⁺

To 2-2 (3.50 g, 6.26 mmol) is added a solution of TFA/DCM (50 mL, 1:1). The mixture is stirred at ambient temperature for 3 h and concentrated. The resultant residue is dissolved in DCM (100 mL), washed with saturated aqueous NaHCO₃, dried over Na₂SO₄, filtered and concentrated. The residue is purified by flash chromatography (eluting with 0-10% MeOH in DCM) to afford a solid, which is recrystallized in absolute EtOH to give the title product (2).

Example 14

Preparation of 1-(4-{7-[5-(2H-Pyrazol-3-yl)-pyridin-2-yloxy]-quinolin-3-ylmethyl}-piperazin-1-yl)-propan-1-one (14)

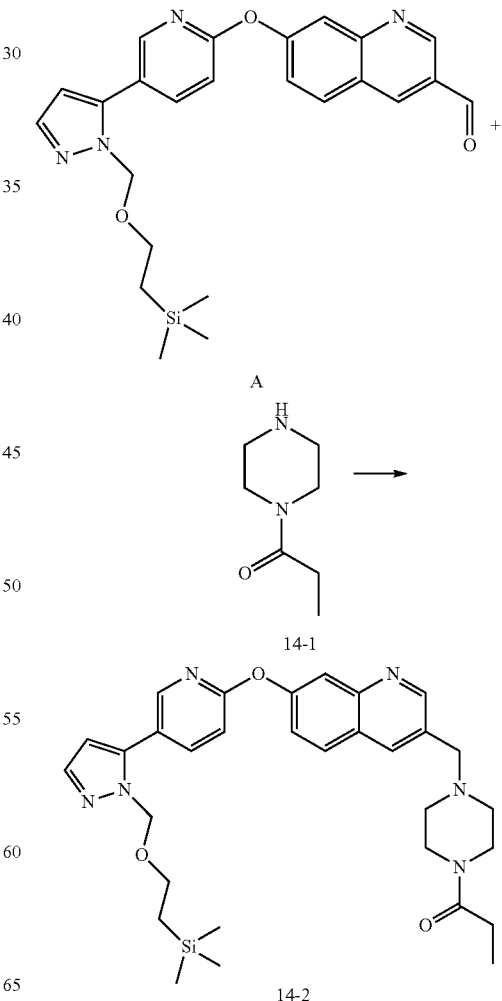

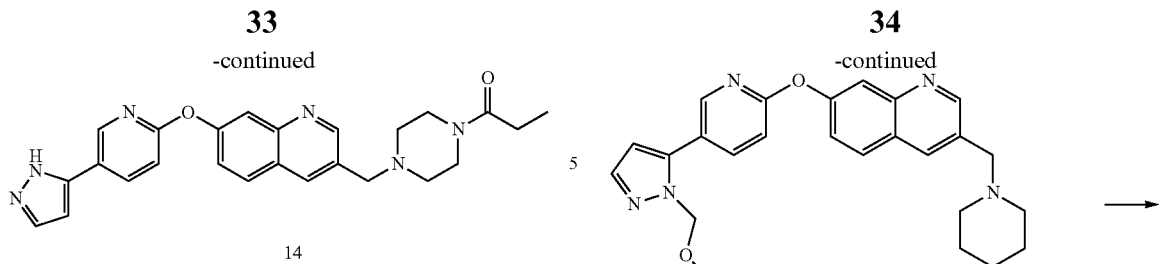

14

To a stirred solution of intermediates A (8.00 g, 17.9 mmol), 14-1 (6.40 g, 35.8 mmol), and triethyl amine (5.00 mL, 35.7 mmol) in DCM (250 mL) is added sodiumtriacetoxyborohydride (6.00 g, 28.3 mmol). The resultant mixture is stirred at ambient temperature for 16 h. The mixture is diluted with DCM (75 mL), and extracted with saturated aqueous NaHCO$_3$. The organic layer is dried over Na$_2$SO$_4$, filtered and concentrated. The residue is purified by flash chromatography (eluting with 0-10% MeOH in DCM) to afford the intermediate 14-2.

To a solution of 14-2 (5.00 g, 10.5 mmol) in DCM (20 mL) is added TFA (20 mL). The mixture is stirred at ambient temperature for 2 h and concentrated. The resultant residue is dissolved in DCM (100 mL), washed with saturated aqueous NaHCO$_3$ (100 mL), dried over Na$_2$SO$_4$, filtered and concentrated. The residue is purified by flash chromatography eluting with a gradient of 0-10% MeOH (+0.5% NH$_4$OH) in DCM to afford a solid, which is triturated with MeCN to give the title product (14).

Example 15

Preparation of 2-Hydroxy-N-methyl-N-(1-{7-[5-(2H-pyrazol-3-yl)-pyridin-2-yloxy]-quinolin-3-ylmethyl}-piperidin-4-yl)-acetamide (15)

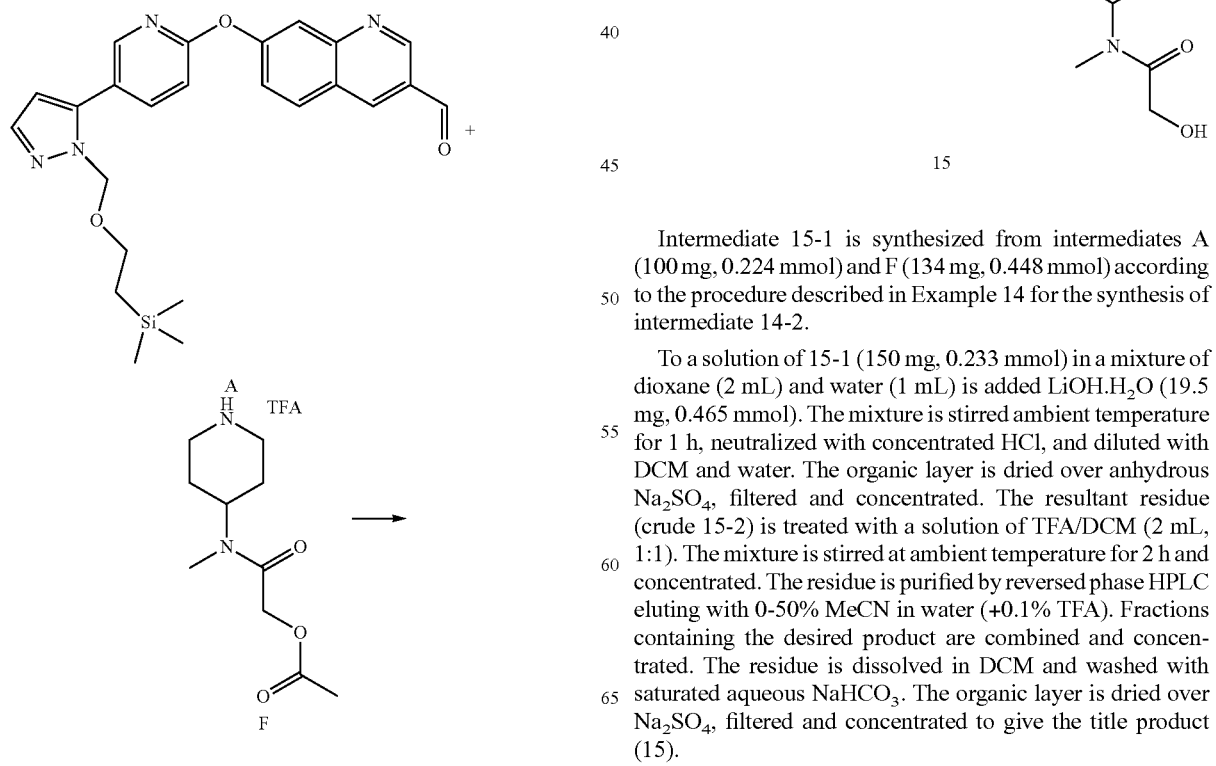

Intermediate 15-1 is synthesized from intermediates A (100 mg, 0.224 mmol) and F (134 mg, 0.448 mmol) according to the procedure described in Example 14 for the synthesis of intermediate 14-2.

To a solution of 15-1 (150 mg, 0.233 mmol) in a mixture of dioxane (2 mL) and water (1 mL) is added LiOH.H$_2$O (19.5 mg, 0.465 mmol). The mixture is stirred ambient temperature for 1 h, neutralized with concentrated HCl, and diluted with DCM and water. The organic layer is dried over anhydrous Na$_2$SO$_4$, filtered and concentrated. The resultant residue (crude 15-2) is treated with a solution of TFA/DCM (2 mL, 1:1). The mixture is stirred at ambient temperature for 2 h and concentrated. The residue is purified by reversed phase HPLC eluting with 0-50% MeCN in water (+0.1% TFA). Fractions containing the desired product are combined and concentrated. The residue is dissolved in DCM and washed with saturated aqueous NaHCO$_3$. The organic layer is dried over Na$_2$SO$_4$, filtered and concentrated to give the title product (15).

The following examples are synthesized using the intermediate A and the appropriate amine reagent (intermediates G through J) according to the above-described procedure for the synthesis of Example 15.

| Ex. | Amine Reagent | Compound Name |
|---|---|---|
| 9 | | 2-Hydroxy-1-[(R)-3-(methyl-{7-[5-(2H-pyrazol-3-yl)-pyridin-2-yloxy]-quinolin-3-ylmethyl}-amino)-pyrrolidin-1-yl]-ethanone |
| 10 | | 2-Hydroxy-1-[(S)-3-(methyl-{7-[5-(2H-pyrazol-3-yl)-pyridin-2-yloxy]-quinolin-3-ylmethyl}-amino)-pyrrolidin-1-yl]-ethanone |
| 11 | | 2-Hydroxy-N-methyl-N-((S)-1-{7-[5-(2H-pyrazol-3-yl)-pyridin-2-yloxy]-quinolin-3-ylmethyl}-pyrrolidin-3-yl)-acetamide |
| 12 | | 2-Hydroxy-N-methyl-N-((R)-1-{7-[5-(2H-pyrazol-3-yl)-pyridin-2-yloxy]-quinolin-3-ylmethyl}-pyrrolidin-3-yl)-acetamide |

Example 16

Preparation of 1-{3-[(Methyl-{7-[5-(2H-pyrazol-3-yl)-pyridin-2-yloxy]-quinolin-3-ylmethyl}-amino)-methyl}-azetidin-1-yl]-ethanone (16)

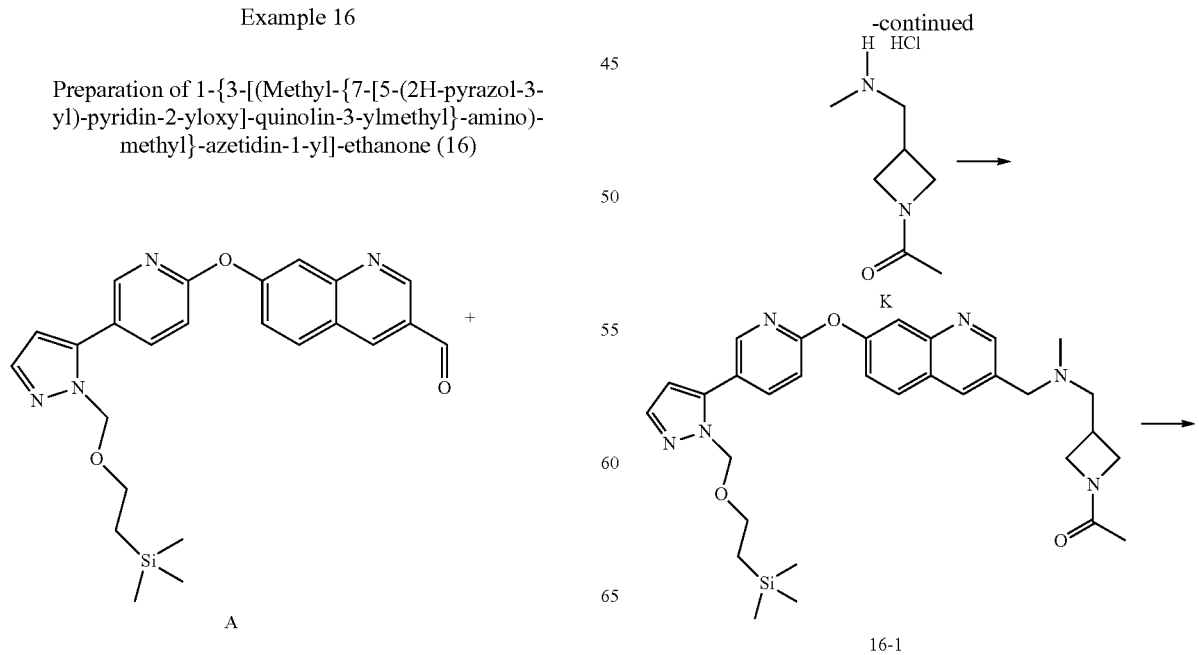

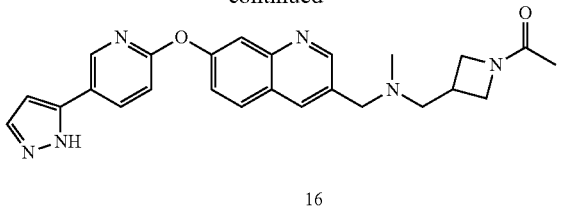

16

A solution of intermediates A (100.0 mg, 0.224 mmol), K (80 mg, 0.448 mmol) and TEA (62.8 mL, 0.448 mmol) in DCM (2 mL) is treated with sodiumtriacetoxyborohydride (94.9 mg, 0.448 mmol). The resultant mixture is stirred at ambient temperature for 24 h and concentrated. The residue is purified by reverse phase HPLC eluting with 0-70% MeCN in water (+0.1% TFA) to give intermediate 16-1.

To 16-1 (125 mg, 0.218 mmol) is added a solution of TFA/DCM (2 mL, 1:1). The mixture is stirred for 2 h and concentrated. The residue is purified by reversed phase HPLC eluting with 0-65% MeCN in water (+0.1% TFA). Fractions containing the desired product are combined and concentrated. The residue is dissolved in DCM and washed with saturated aqueous $NaHCO_3$. The organic layer is dried over $Na_2SO_4$, filtered and concentrated to give the title product (16).

The following examples are synthesized using intermediate A and the appropriate amine reagent (free base or the salt form) according to the above-described procedure for the synthesis of Example 16. Generally, for the syntheses that utilize amine salts, an equivalent of triethylamine is added prior to addition of sodium triacetoxyborohyide.

| Ex. | Amine Reagent | Compound Name |
|---|---|---|
| 3 | | 1-{7-[5-(2H-Pyrazol-3-yl)-pyridin-2-yloxy]-quinolin-3-ylmethyl}-azetidin-3-ol |
| 4 | | 2-Methoxy-1-(4-{7-[5-(2H-pyrazol-3-yl)-pyridin-2-yloxy]-quinolin-3-ylmethyl}-piperazin-1-yl)-ethanone |
| 5 | | (S)-3-Hydroxy-1-(1-{7-[5-(2H-pyrazol-3-yl)-pyridin-2-yloxy]-quinolin-3-ylmethyl}-piperidin-4-yl)-pyrrolidin-2-one |
| 6 | | 3-(1-{7-[5-(2H-Pyrazol-3-yl)-pyridin-2-yloxy]-quinolin-3-ylmethyl}-piperidin-4-yl)-oxazolidin-2-one |
| 7 | | 1-{7-[5-(2H-Pyrazol-3-yl)-pyridin-2-yloxy]-quinolin-3-ylmethyl}-piperidin-4-ol |
| 8 | | 3-Methyl-1-{7-[5-(2H-pyrazol-3-yl)-pyridin-2-yloxy]-quinolin-3-ylmethyl}-azetidin-3-ol |
| 13 | | (S)-1-{7-[5-(2H-Pyrazol-3-yl)-pyridin-2-yloxy]-quinolin-3-ylmethyl}-pyrrolidin-3-ol |
| 17 | | (R)-1-{7-[5-(2H-Pyrazol-3-yl)-pyridin-2-yloxy]-quinolin-3-ylmethyl}-pyrrolidin-3-ol |
| 18 | | (S)-2-Hydroxy-1-(4-{7-[5-(2H-pyrazol-3-yl)-pyridin-2-yloxy]-quinolin-3-ylmethyl}-piperazin-1-yl)-propan-1-one |
| 19 | | 1-{7-[5-(2H-Pyrazol-3-yl)-pyridin-2-yloxy]-quinolin-3-ylmethyl}-piperidine-4-carboxylic acid dimethylamide |
| 20 | | 2-Hydroxy-2-methyl-1-(4-{7-[5-(2H-pyrazol-3-yl)-pyridin-2-yloxy]-quinolin-3-ylmethyl}-piperazin-1-yl)-propan-1-one |
| 21 | | 2,2-Dimethyl-1-(4-{7-[5-(2H-pyrazol-3-yl)-pyridin-2-yloxy]-quinolin-3-ylmethyl}-piperazin-1-yl)-propan-1-one |
| 22 | | Cyclopropyl-(4-{7-[5-(2H-pyrazol-3-yl)-pyridin-2-yloxy]-quinolin-3-ylmethyl}-piperazin-1-yl)-methanone |
| 23 | | 2-Methyl-1-(4-{7-[5-(2H-pyrazol-3-yl)-pyridin-2-yloxy]-quinolin-3-ylmethyl}-piperazin-1-yl)-propan-1-one |

TABLE 2

Mass spectral and HPLC data for compounds 1-23.

| Ex. | Obs. Mass (m/z) | R.T. (min) |
|---|---|---|
| 1 | 445.2 | 2.46 |
| 2 | 429.4 | 2.49 |
| 3 | 374.4 | 2.54 |
| 4 | 459.3 | 2.57 |
| 5 | 485.3 | 2.55 |
| 6 | 471.3 | 2.58 |
| 7 | 402.3 | 2.55 |

TABLE 2-continued

Mass spectral and HPLC data for compounds 1-23.

| Ex. | Obs. Mass (m/z) | R.T. (min) |
|---|---|---|
| 8 | 388.3 | 2.51 |
| 9 | 459.3 | 0.35 |
| 10 | 458.9 | 2.6 |
| 11 | 459.3 | 0.35 |
| 12 | 458.9 | 2.63 |
| 13 | 388.3 | 0.35 |
| 14 | 443 | 2.51 |
| 15 | 473.3 | 2.49 |
| 16 | 443.2 | 2.64 |
| 17 | 388.1 | 2.63 |
| 18 | 459.3 | 2.49 |
| 19 | 457.4 | 2.53 |
| 20 | 473.3 | 2.47 |
| 21 | 471.3 | 2.56 |
| 22 | 455.3 | 2.5 |
| 23 | 457.4 | 2.5 |

Assessment of Biological Properties

The compounds of the invention are assessed for the ability to interact with human $LTA_4$ hydrolase in an enzymatic assay that measures the ability of the enzyme to cleave the peptide bond of arginyl-aminomethylcoumarin (Arg-AMC). $LTA_4H$ Enzyme (1 nM final), Arg-AMC substrate (50 µM final), and compound are combined in a reaction buffer (50 mM Tris-HCl (pH 7.5), 100 mM KCl, 0.5% bovine serum albumin) at room temperature for 1 h. The formation of product is assessed by measuring the fluorescence of aminomethylcoumarin product (excitation wavelength 380 nm/emission wavelength 460 nm). In general, the preferred potency range ($IC_{50}$) of compounds in the $LTA_4H$ Enzyme assay is between 0.1 nM to 10 µM, the more preferred potency range is 0.1 nM to 0.1 µM, and the most preferred potency range is 0.1 nM to 10 nM.

TABLE 3

$IC_{50}$ values of $LTA_4H$ Enzyme assay.

| Ex. | Peptidase $IC_{50}$ (nM) |
|---|---|
| 1 | 0.69 |
| 2 | 0.6 |
| 3 | 4.0 |
| 4 | 1.4 |
| 5 | 2.6 |
| 6 | 1.9 |
| 7 | 3.7 |
| 8 | 2.4 |
| 9 | 0.88 |
| 10 | 1.3 |
| 11 | 2.6 |
| 12 | 1.8 |
| 13 | 2.5 |
| 14 | 0.44 |
| 15 | 3.5 |
| 16 | 1.1 |
| 17 | 1.7 |
| 18 | 1.1 |
| 19 | 1.5 |
| 20 | 1.6 |
| 21 | 1.7 |
| 22 | 0.93 |
| 23 | 0.54 |

The compounds of the invention are additionally tested in a human whole blood (HWB) assay to determine their ability to inhibit the synthesis of LTB4 in a cellular system. Compounds are combined with heparinized human whole blood and incubated for 15 minutes at 37° C. Calcimycin (20 µM final, prepared in phosphate-buffered saline, pH 7.4) is then added and the mixture is incubated for another 30 minutes at 37° C. The samples are centrifuged for 5 min at low speed (1500×g) and the plasma layer is removed. Plasma LTB4 concentrations are then measured using an antibody-based homogenous time-resolved fluorescence method (CisBio, Bedford, Mass.). In general, the preferred potency range (IC50) of compounds in the HWB assay is between 10 nM to 10 µM, the more preferred potency range is 10 nM to 1 µM, and the most preferred potency range is 10 nM to 100 nM. The potencies of representative compounds of the invention in the WHB assays are shown in Table 4.

TABLE 4

$IC_{50}$ values of LTB4 production inhibition assay in human whole blood (HWB).

| Ex. | HWB $IC_{50}$ (nM) |
|---|---|
| 1 | 160 |
| 2 | 150 |
| 3 | 430 |
| 4 | 170 |
| 5 | 370 |
| 6 | 270 |
| 7 | 500 |
| 8 | 410 |
| 9 | 150 |
| 10 | 140 |
| 11 | 250 |
| 12 | 180 |
| 13 | 220 |
| 14 | 86 |
| 15 | 380 |
| 16 | 110 |
| 17 | 230 |
| 18 | 180 |
| 19 | 480 |
| 20 | 230 |
| 21 | 740 |
| 22 | 230 |
| 23 | 160 |

Methods of Use

The compounds of the invention are effective inhibitors of leukotriene $A_4$ hydrolase ($LTA_4H$) and thus inhibit leukotriene production. Therefore, in one embodiment of the invention, there is provided methods of treating leukotriene-mediated disorders using compounds of the invention. In another embodiment, there is provided methods of treating cardiovascular, inflammatory, allergic, pulmonary and fibrotic diseases, renal diseases and cancer using compounds of the invention.

In one embodiment, the invention relates to a compound of the invention for use as a medicament for the treatment leukotriene-mediated disorders. In another embodiment, the invention relates to a compound of the invention for use in a method of treating cardiovascular, inflammatory, allergic, pulmonary and fibrotic diseases, renal diseases and cancer.

In one embodiment, the invention relates to the use of a compound of the invention for the preparation of a medicament for the treatment leukotriene-mediated disorders. In another embodiment, the invention relates to the use of a compound of the invention, for the preparation of a medicament for treating cardiovascular, inflammatory, allergic, pulmonary and fibrotic diseases, renal diseases and cancer.

In one embodiment, the invention relates to a compound of the invention for use as a medicament for the treatment leukotriene-mediated disorders. In another embodiment, the invention relates to a compound of the invention for use in a method of treating cardiovascular, inflammatory, allergic, pulmonary and fibrotic diseases, renal diseases and cancer.

Without wishing to be bound by theory, by inhibiting the activity of $LTA_4H$, the compounds of the invention block the production of $LTB_4$ resulting from the oxidation of arachidonic acid by 5-LO and subsequent metabolism. Thus, the inhibition of $LTA_4H$ activity is an attractive means for preventing and treating a variety of diseases mediated by $LTB_4$. These include:

Cardiovascular diseases including atherosclerosis, myocardial infarction, stroke, aortic aneurysm, sickle cell crisis, ischemia-reperfusion injury, pulmonary arterial hypertension and sepsis;

Allergic diseases including asthma, allergic rhinitis, rhinosinusitis, atopic dermatitis and urticaria;

Fibrotic diseases including airway remodeling in asthma, idiopathic pulmonary fibrosis, scleroderma, asbestosis;

Pulmonary syndromes including adult respiratory distress syndrome, viral bronchiolitis, obstructive sleep apnea, chronic obstructive pulmonary disease, cystic fibrosis, and bronchopulmonary dysplasia;

Inflammatory diseases including rheumatoid arthritis, osteoarthritis, gout, glomerulonephritis, interstitial cystitis, psoriasis, inflammatory bowel disease systemic lupus erythematosus, transplant rejection, inflammatory allergic ocular diseases, atopic dermatitis, allergy, asthma, autoimmune diseases, Crohn's disease, cystic fibrosis, diabetic nephropathy, diabetic retinopathy, ulcerative colitis, and steatohepatitis;

Cancer including solid tumors, leukemias and lymphomas; and Renal diseases such as glomerulonephritis.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased antagonist activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by *Remington: The Science and Practice of Pharmacy,* 20th Edition, A. Gennaro (ed.), Lippincott Williams & Wilkins, 2000; *Handbook of Pharmaceutical Additives*, Michael & Irene Ash (eds.), Gower, 1995; *Handbook of Pharmaceutical Excipients*, A. H. Kibbe (ed.), American Pharmaceutical Ass'n, 2000; H. C. Ansel and N. G. Popovish, *Pharmaceutical Dosage Forms and Drug Delivery Systems,* 5th ed., Lea and Febiger, 1990; each of which is incorporated herein by reference in their entireties to better describe the state of the art.

Combination Therapy

The compounds of the invention may be administered alone or in combination with at least one additional active agent. Thus, in one embodiment, the invention relates to a pharmaceutical composition comprising one or more compounds of the invention in combination with at least one additional agent. In another embodiment, the invention relates a method of treating diseases mediated by $LTB_4$, the method comprising administering a therapeutically effective amount of one or more compounds of the invention in combination with a pharmaceutically effective amount of at least one additional agent.

Nonlimiting examples of additional active agents include statins (or HMG-CoA reductase inhibitors); cholesterol ester transfer protein (CETP) inhibitors (or antagonists); fibrates, niacin derivatives, Lp-PLA2-inhibitors (e.g., darapladib, varespladib), antiplatelets and anticoagulants.

In one embodiment, the additional active agent is a statin. In another embodiment, the additional active agent is a statin selected from the group consisting of atorvastatin, fluvastatin, lovastatin, pitavastatin, pravastatin, rosuvastatin, and simvastatin.

In one embodiment, the additional active agent is a CETP inhibitor. In another embodiment, the additional active agent is a CETP inhibitor selected from the group consisting of anacetrapib, dalcetrapib, evacetrapib, TA-8995 (Mitsubishi Tanabe Pharma), ATH-03 (Affris), DRL-17822 (Dr. Reddy's). In yet another embodiment, the additional active is selected from the group consisting of dalcetrapib and anacetrapib.

As one of skill in the art would expect, the forms of the compounds of the invention utilized in a particular pharmaceutical formulation will be selected (e.g., salts) that possess suitable physical characteristics (e.g., water solubility) that are required for the formulation to be efficacious.

As one of skill in the art would expect, the forms of the compounds of the invention utilized in a particular pharmaceutical formulation will be selected (e.g., salts) that possess suitable physical characteristics (e.g., water solubility) that are required for the formulation to be efficacious.

What is claimed is:

1. A compound of formula (I):

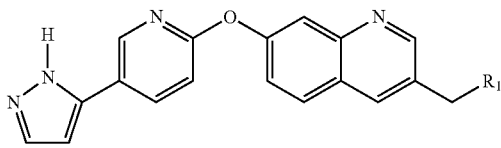

or a pharmaceutically acceptable salt thereof, wherein:
$R^1$ is:
(a) a group of formula —N($R^2$)($R^3$), wherein
$R^2$ is selected from the group consisting of hydrogen, —($C_1$-$C_6$)alkyl, and —($C_3$-$C_6$)cycloalkyl;
$R^3$ is selected from the group consisting of hydrogen, —($C_1$-$C_6$)alkyl, —($C_3$-$C_6$)cycloalkyl, and -(4- to 7-membered)heterocyclyl,
wherein each of said —($C_1$-$C_6$)alkyl, —($C_3$-$C_6$)cycloalkyl, and -(4- to 7-membered)heterocyclyl of said $R^3$ may optionally be substituted by 1 to 3 groups independently selected from the group consisting of $R^4$, —(($C_1$-$C_6$)alkylene)-$R^4$, —C(O)—($C_1$-$C_6$)alkyl, —C(O)—($C_3$-$C_6$)cycloalkyl, and —C(O)—(($C_1$-$C_6$)alkylene)-$R^4$;
$R^4$ is selected from the group consisting of halo, —OH, =O, —$NH_2$, —NH($C_1$-$C_6$)alkyl, —N(($C_1$-$C_6$)alky)$_2$, —($C_1$-$C_6$)alkyl, —O($C_1$-$C_6$)alkyl, —($C_3$-$C_6$)cycloalkyl, and -(4- to 7-membered)heterocyclyl);
wherein each of said $R^4$ may optionally be substituted by 1 to 3 groups independently selected from the group consisting of —O($C_1$-$C_6$)alkyl, and —($C_3$-$C_6$)cycloalkyl;
or
(b) a 4- to 9-membered N-heterocyclic ring of formula:

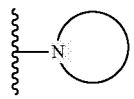

wherein said 4- to 9-membered N-heterocyclic ring optionally comprises one to three additional heteroring atoms selected from the group consisting of nitrogen, oxygen and sulfur atoms; and wherein said 4- to 9-membered N-heterocyclic ring is optionally substituted by 1 to 3 groups independently selected from the group consisting of $R^5$, —(($C_1$-$C_6$)alkylene)-$R^5$, —C(O)—($C_1$-$C_6$)alkyl, —C(O)—($C_3$-$C_6$)cycloalkyl, —C(O)—(($C_1$-$C_6$)alkylene)-$R^5$, —C(O)—N($R^6$)—(($C_1$-$C_6$)alkylene)-$R^5$, —C(O)—N($R^6$)($R^6$) and -(4- to 7-membered)heterocyclyl) optionally substituted by 1 to 3 $R^5$ groups;
each $R^5$ is independently selected from the group consisting of halo, —OH, =O, —N($R^6$)$_2$, —N($R^6$)(C(O)—$R^6$), —($C_1$-$C_6$)alkyl, —O($C_1$-$C_6$)alkyl, —($C_3$-$C_6$)cycloalkyl, and -(4- to 7-membered)heterocyclyl); and
each $R^6$ is independently selected from the group consisting of hydrogen and —($C_1$-$C_6$)alkyl optionally substituted by —OH.

2. The compound of claim 1, or a pharmaceutically acceptable salt thereof, wherein $R^1$ is a group of formula —N($R^2$)($R^3$), and wherein $R^2$ is —($C_1$-$C_6$)alkyl.

3. The compound of claim 1, or a pharmaceutically acceptable salt thereof, wherein $R^1$ is a group of formula —N($R^2$)($R^3$), and wherein $R^3$ is a -(4- to 7-membered)heterocyclyl optionally substituted by 1 to 3 groups independently selected from the group consisting of $R^4$, —(($C_1$-$C_6$)alkylene)-$R^4$, —C(O)—($C_1$-$C_6$)alkyl, —C(O)—($C_3$-$C_6$)cycloalkyl, and —C(O)—(($C_1$-$C_6$)alkylene)-$R^4$.

4. The compound of claim 1, or a pharmaceutically acceptable salt thereof, wherein $R^1$ is a group of formula —N($R^2$)($R^3$), and wherein
$R^2$ is —($C_1$-$C_6$)alkyl; and
$R^3$ is pyrrolidinyl optionally substituted by 1 to 3 groups independently selected from the group consisting of —OH and —C(O)—($C_1$-$C_6$)alkylene)-OH.

5. The compound of claim 1, or a pharmaceutically acceptable salt thereof, wherein $R^1$ is a group of formula —N($R^2$)($R^3$), and wherein
$R^2$ is methyl; and
$R^3$ is pyrrolidinyl substituted by —C(O)—($C_1$-$C_6$)alkylene)-OH.

6. The compound of claim 1, or a pharmaceutically acceptable salt thereof, wherein $R^1$ is a group of formula —N($R^2$)($R^3$), and wherein
$R^2$ is —($C_1$-$C_6$)alkyl, and
$R^3$ is —($C_1$-$C_6$)alkyl optionally substituted by 1 to 3 groups independently selected from the group consisting of $R^4$, —(($C_1$-$C_6$)alkylene)-$R^4$, —C(O)—($C_1$-$C_6$)alkyl, and —C(O)—(($C_1$-$C_6$)alkylene)-$R^4$.

7. The compound of claim 1, or a pharmaceutically acceptable salt thereof, wherein $R^1$ is a group of formula —N($R^2$)($R^3$), and wherein
$R^2$ is —($C_1$-$C_6$)alkyl, and
$R^3$ is —($C_1$-$C_6$)alkyl optionally substituted by a -(4- to 7-membered)heterocyclyl), wherein said -(4- to 7-membered)heterocyclyl) is optionally substituted by 1 to 3 groups independently selected from the group consisting of —C(O)—($C_1$-$C_6$)alkyl, and —C(O)—($C_3$-$C_6$)cycloalkyl.

8. The compound of claim 1, or a pharmaceutically acceptable salt thereof, wherein $R^1$ is a group of formula —N($R^2$)($R^3$), and wherein
$R^2$ is methyl, and
$R^3$ is methyl substituted by a -(4- to 7-membered)heterocyclyl), wherein said -(4- to 7-membered)heterocyclyl) is substituted by 1 to 2 groups independently selected from the group consisting of —C(O)—($C_1$-$C_6$)alkyl.

9. The compound of claim 1, or a pharmaceutically acceptable salt thereof, wherein $R^1$ is a 4- to 9-membered N-heterocyclic ring, and wherein said 4- to 9-membered N-heterocyclic ring is optionally substituted by 1 to 3 groups independently selected from the group consisting of $R^5$, —(($C_1$-$C_6$)alkylene)-$R^5$, —C(O)—($C_1$-$C_6$)alkyl, —C(O)—($C_3$-$C_6$)cycloalkyl, —C(O)—(($C_1$-$C_6$)alkylene)-$R^5$, —C(O)—N($R^6$)—(($C_1$-$C_6$)alkylene)-$R^5$, —C(O)—N($R^6$)($R^6$), and -(4- to 7-membered)heterocyclyl).

10. The compound of claim 1, or a pharmaceutically acceptable salt thereof, wherein $R^1$ is a 4- to 9-membered N-heterocyclic ring selected from the group consisting of azetidinyl, pyrrolidinyl, piperidinyl, and piperazinyl; wherein each of said azetidinyl, pyrrolidinyl, piperidinyl, and piperazinyl is optionally substituted by 1 to 3 groups independently selected from the group consisting of $R^5$, —(($C_1$-$C_6$)alkylene)-$R^5$, —C(O)—($C_1$-$C_6$)alkyl, —C(O)—($C_3$-$C_6$)cycloalkyl, —C(O)—(($C_1$-$C_6$)alkylene)-$R^5$, —C(O)—N($R^6$)—(($C_1$-$C_6$)alkylene)-$R^5$, —C(O)—N($R^6$)($R^6$), and -(4- to 7-membered)heterocyclyl).

11. The compound of claim 1, or a pharmaceutically acceptable salt thereof, wherein $R^1$ is selected from the group consisting of:
- an azetidinyl substituted by 1 to 3 groups selected from the group consisting of —OH, —($C_1$-$C_6$)alkyl and —C(O)—($C_1$-$C_6$)alkyl;
- a pyrrolidinyl substituted by 1 to 3 groups selected from the group consisting of —OH, —C(O)—(($C_1$-$C_6$)alkylene)-OH and —N(($C_1$-$C_6$)alkyl)-C(O)—($C_1$-$C_6$)alkylene)-OH;
- a piperidinyl substituted by 1 to 3 groups selected from the group consisting of —OH, —C(O)—(($C_1$-$C_6$)alkylene)-OH, —C(O)—N(($C_1$-$C_6$)alkyl)$_2$, —N(($C_1$-$C_6$)alkyl)-C(O)—($C_1$-$C_6$)alkylene)-OH, pyrollidinonyl optionally substituted by —OH, oxazolidinonyl; and
- a piperazinyl substituted by 1 to 3 groups selected from the group consisting of —C(O)—($C_1$-$C_6$)alkyl, —C(O)—($C_3$-$C_6$)cycloalkyl, —C(O)—(($C_1$-$C_6$)alkylene)-OH, and —C(O)—(($C_1$-$C_6$)alkylene)-O—($C_1$-$C_6$)alkyl.

12. A compound selected from the group consisting of:
2-Hydroxy-1-(4-{7-[5-(2H-pyrazol-3-yl)-pyridin-2-yloxy]-quinolin-3-ylmethyl}-piperazin-1-yl)-ethanone;
1-(4-{7-[5-(2H-Pyrazol-3-yl)-pyridin-2-yloxy]-quinolin-3-ylmethyl}-piperazin-1-yl)-ethanone;
1-{7-[5-(2H-Pyrazol-3-yl)-pyridin-2-yloxy]-quinolin-3-ylmethyl}-azetidin-3-ol
2-Methoxy-1-(4-{7-[5-(2H-pyrazol-3-yl)-pyridin-2-yloxy]-quinolin-3-ylmethyl}-piperazin-1-yl)-ethanone;
(S)-3-Hydroxy-1-(1-{7-[5-(2H-pyrazol-3-yl)-pyridin-2-yloxy]-quinolin-3-ylmethyl}-piperidin-4-yl)-pyrrolidin-2-one;
3-(1-{7-[5-(2H-Pyrazol-3-yl)-pyridin-2-yloxy]-quinolin-3-ylmethyl}-piperidin-4-yl)-oxazolidin-2-one;
1-{7-[5-(2H-Pyrazol-3-yl)-pyridin-2-yloxy]-quinolin-3-ylmethyl}-piperidin-4-ol;
3-Methyl-1-{7-[5-(2H-pyrazol-3-yl)-pyridin-2-yloxy]-quinolin-3-ylmethyl}-azetidin-3-ol;
2-Hydroxy-1-[(R)-3-(methyl-{7-[5-(2H-pyrazol-3-yl)-pyridin-2-yloxy]-quinolin-3-ylmethyl}-amino)-pyrrolidin-1-yl]-ethanone; and
2-Hydroxy-1-[(S)-3-(methyl-{7-[5-(2H-pyrazol-3-yl)-pyridin-2-yloxy]-quinolin-3-ylmethyl}-amino)-pyrrolidin-1-yl]-ethanone;
2-Hydroxy-N-methyl-N—((S)-1-{7-[5-(2H-pyrazol-3-yl)-pyridin-2-yloxy]-quinolin-3-ylmethyl}-pyrrolidin-3-yl)-acetamide;
2-Hydroxy-N-methyl-N—((R)-1-{7-[5-(2H-pyrazol-3-yl)-pyridin-2-yloxy]-quinolin-3-ylmethyl}-pyrrolidin-3-yl)-acetamide;
(S)-1-{7-[5-(2H-Pyrazol-3-yl)-pyridin-2-yloxy]-quinolin-3-ylmethyl}-pyrrolidin-3-ol;
1-(4-{7-[5-(2H-Pyrazol-3-yl)-pyridin-2-yloxy]-quinolin-3-ylmethyl}-piperazin-1-yl)-propan-1-one;
2-Hydroxy-N-methyl-N-(1-{7-[5-(2H-pyrazol-3-yl)-pyridin-2-yloxy]-quinolin-3-ylmethyl}-piperidin-4-yl)-acetamide;
1-{3-[(Methyl-{7-[5-(2H-pyrazol-3-yl)-pyridin-2-yloxy]-quinolin-3-ylmethyl}-amino)-methyl]-azetidin-1-yl}-ethanone;
(R)-1-{7-[5-(2H-Pyrazol-3-yl)-pyridin-2-yloxy]-quinolin-3-ylmethyl}-pyrrolidin-3-ol;
(S)-2-Hydroxy-1-(4-{7-[5-(2H-pyrazol-3-yl)-pyridin-2-yloxy]-quinolin-3-ylmethyl}-piperazin-1-yl)-propan-1-one;
1-{7-[5-(2H-Pyrazol-3-yl)-pyridin-2-yloxy]-quinolin-3-ylmethyl}-piperidine-4-carboxylic acid dimethylamide;
2-Hydroxy-2-methyl-1-(4-{7-[5-(2H-pyrazol-3-yl)-pyridin-2-yloxy]-quinolin-3-ylmethyl}-piperazin-1-yl)-propan-1-one;
2,2-Dimethyl-1-(4-{7-[5-(2H-pyrazol-3-yl)-pyridin-2-yloxy]-quinolin-3-ylmethyl}-piperazin-1-yl)-propan-1-one;
Cyclopropyl-(4-{7-[5-(2H-pyrazol-3-yl)-pyridin-2-yloxy]-quinolin-3-ylmethyl}-piperazin-1-yl)-methanone; and
2-Methyl-1-(4-{7-[5-(2H-pyrazol-3-yl)-pyridin-2-yloxy]-quinolin-3-ylmethyl}-piperazin-1-yl)-propan-1-one;
and pharmaceutically acceptable salts thereof.

13. A pharmaceutical composition comprising one or more compounds of claim 1, or a pharmaceutically acceptable salt thereof, and a pharmaceutically acceptable carrier or excipient.

14. The pharmaceutical composition of claim 13, further comprising at least one additional pharmacologically active substance.

15. A method of inhibiting leukotriene $A_4$ hydrolase ($LTA_4H$) comprising administering a pharmaceutically effective amount of a compound of claim 1, or a pharmaceutically acceptable salt thereof, to a patient in need thereof.

16. A method of treating a cardiovascular disease or an inflammatory disease comprising administering a pharmaceutically effective amount of a compound of claim 1, or a pharmaceutically acceptable salt thereof, to a patient in need thereof.

* * * * *